(12) United States Patent
Nakashita et al.

(10) Patent No.: US 9,775,751 B2
(45) Date of Patent: Oct. 3, 2017

(54) ABSORBENT ARTICLE

(71) Applicant: UNICHARM CORPORATION, Shikokuchuo-shi, Ehime (JP)

(72) Inventors: Masashi Nakashita, Kanonji (JP); Ichiro Wada, Kanonji (JP); Yuki Noda, Kanonji (JP); Akira Hashino, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/381,948

(22) PCT Filed: Feb. 21, 2013

(86) PCT No.: PCT/JP2013/054382
§ 371 (c)(1),
(2) Date: Aug. 28, 2014

(87) PCT Pub. No.: WO2013/129236
PCT Pub. Date: Sep. 6, 2013

(65) Prior Publication Data
US 2015/0032074 A1   Jan. 29, 2015

(30) Foreign Application Priority Data

Feb. 29, 2012   (JP) .................. 2012-044354

(51) Int. Cl.
*A61F 13/51* (2006.01)
*A61F 13/84* (2006.01)
(Continued)

(52) U.S. Cl.
CPC ...... *A61F 13/472* (2013.01); *A61F 13/51104* (2013.01); *A61F 13/51113* (2013.01);
(Continued)

(58) Field of Classification Search
CPC .......... A61F 13/51104; A61F 13/51108; A61F 13/51113; A61F 13/8405;
(Continued)

(56) References Cited

U.S. PATENT DOCUMENTS 3,929,135 A   12/1975 Thompson
4,588,630 A   5/1986 Shimalla
(Continued)

FOREIGN PATENT DOCUMENTS

CN    1432352        7/2003
EP    1250940 A1    10/2002
(Continued)

OTHER PUBLICATIONS

Atsushi Fujita, "Prediction of Organic Compounds and Organic Conceptual Diagram", Kagaku no Ryoiki (Region of Chemistry), Oct. 1957, p. 719-725, vol. 11, No. 10.
(Continued)

*Primary Examiner* — Lynne Anderson
(74) *Attorney, Agent, or Firm* — Hauptman Ham, LLP

(57) ABSTRACT

An object of the present disclosure is to provide an absorbent article without a sticky feel on the top sheet and with a smooth top sheet, not only when a large amount of menstrual blood has been absorbed, but even when a small amount of menstrual blood has been absorbed. The absorbent article of the present disclosure is as follows. An absorbent article comprising a liquid-permeable top sheet, a liquid-impermeable back sheet and an absorbent body between the liquid-permeable top sheet and liquid-impermeable back sheet, wherein the liquid-permeable top sheet comprises a blood slipping agent having a kinematic viscosity of 0.01 to 80 mm$^2$/s at 40° C., a water holding percentage of 0.01 to 4.0
(Continued)

mass %, and a weight-average molecular weight of less than 1,000, on at least the projection in an excretory opening contact region.

10 Claims, 4 Drawing Sheets

(51) Int. Cl.
    *A61F 13/472*     (2006.01)
    *B32B 3/30*     (2006.01)
    *A61F 13/511*     (2006.01)
    *A61L 15/20*     (2006.01)
    *A61L 15/50*     (2006.01)
    *B32B 5/02*     (2006.01)
    *B32B 5/26*     (2006.01)

(52) U.S. Cl.
    CPC .......... *A61F 13/8405* (2013.01); *A61L 15/20* (2013.01); *A61L 15/50* (2013.01); *B32B 3/30* (2013.01); *B32B 5/022* (2013.01); *B32B 5/024* (2013.01); *B32B 5/26* (2013.01); *A61F 2013/8455* (2013.01); *B32B 2250/20* (2013.01); *B32B 2262/0253* (2013.01); *B32B 2262/0276* (2013.01); *B32B 2262/062* (2013.01); *B32B 2307/726* (2013.01); *B32B 2307/73* (2013.01); *B32B 2555/02* (2013.01)

(58) Field of Classification Search
    CPC .. A61F 2013/15284; A61F 2013/51117; A61F 2013/51066; A61F 2013/51069; A61F 2013/8455; A61F 2013/8461
    See application file for complete search history.

(56) References Cited

U.S. PATENT DOCUMENTS

| | | | |
|---|---|---|---|
| 4,759,754 A | 7/1988 | Korpman | |
| 5,078,710 A | 1/1992 | Suda et al. | |
| 5,334,176 A | 8/1994 | Buenger et al. | |
| 5,344,416 A | 9/1994 | Niihara | |
| 5,591,149 A | 1/1997 | Cree et al. | |
| 5,609,587 A * | 3/1997 | Roe | A61K 8/0208 |
| | | | 604/359 |
| 5,614,283 A | 3/1997 | Potnis et al. | |
| 5,650,214 A | 7/1997 | Anderson et al. | |
| 5,693,337 A * | 12/1997 | Suzuki | A61K 9/0014 |
| | | | 424/450 |
| 5,968,025 A | 10/1999 | Roe et al. | |
| 6,120,488 A * | 9/2000 | VanRijswijck | A61F 13/494 |
| | | | 604/364 |
| 6,153,209 A | 11/2000 | Vega et al. | |
| 6,730,819 B1 | 5/2004 | Pesce | |
| 7,781,641 B2 * | 8/2010 | Kasai | A61F 13/511 |
| | | | 604/360 |
| 8,283,515 B2 * | 10/2012 | Lagerstedt-Eidrup | A61F 13/511 |
| | | | 424/76.5 |
| 8,865,965 B2 * | 10/2014 | Sato | A61F 13/51104 |
| | | | 604/367 |
| 2001/0029141 A1 | 10/2001 | Mizutani et al. | |
| 2002/0058917 A1 * | 5/2002 | Hisanaka | A61L 15/20 |
| | | | 604/385.01 |
| 2003/0088222 A1 | 5/2003 | Yoshimasa et al. | |
| 2003/0149410 A1 | 8/2003 | Kudo et al. | |
| 2003/0198784 A1 | 10/2003 | Mizutani et al. | |
| 2004/0102750 A1 * | 5/2004 | Jameson | A61F 13/511 |
| | | | 604/367 |
| 2006/0135920 A1 * | 6/2006 | Virgilio | A61F 13/511 |
| | | | 604/359 |
| 2006/0184150 A1 | 8/2006 | Noel | |
| 2006/0276767 A1 | 12/2006 | Ueminami et al. | |
| 2007/0219515 A1 | 9/2007 | Marsh et al. | |
| 2007/0298213 A1 | 12/2007 | Noda et al. | |
| 2007/0298214 A1 | 12/2007 | Noda et al. | |
| 2007/0298220 A1 | 12/2007 | Noda et al. | |
| 2007/0298667 A1 | 12/2007 | Noda et al. | |
| 2007/0298671 A1 | 12/2007 | Noda et al. | |
| 2007/0299416 A1 | 12/2007 | Noda et al. | |
| 2008/0010795 A1 | 1/2008 | Mizutani et al. | |
| 2008/0044622 A1 | 2/2008 | Noda et al. | |
| 2008/0044628 A1 | 2/2008 | Noda et al. | |
| 2008/0045915 A1 | 2/2008 | Noda et al. | |
| 2008/0085399 A1 | 4/2008 | Noda et al. | |
| 2008/0132136 A1 | 6/2008 | Uematsu et al. | |
| 2008/0200894 A1 | 8/2008 | Gatto et al. | |
| 2009/0186791 A1 * | 7/2009 | Matsushita | A61K 8/361 |
| | | | 510/130 |
| 2009/0221978 A1 | 9/2009 | Gatto et al. | |
| 2009/0282660 A1 | 11/2009 | Noda et al. | |
| 2010/0008875 A1 * | 1/2010 | Oguchi | A61K 8/35 |
| | | | 424/60 |
| 2010/0069874 A1 | 3/2010 | Noda et al. | |
| 2010/0137824 A1 | 6/2010 | Uematsu et al. | |
| 2010/0151054 A1 * | 6/2010 | Nishioku | A61K 8/06 |
| | | | 424/678 |
| 2010/0191207 A1 | 7/2010 | Oba et al. | |
| 2011/0319851 A1 | 12/2011 | Kudo et al. | |
| 2012/0045620 A1 | 2/2012 | Oba et al. | |
| 2012/0141742 A1 | 6/2012 | Yamaguchi et al. | |
| 2012/0177889 A1 | 7/2012 | Uematsu et al. | |
| 2012/0196091 A1 | 8/2012 | Mizutani et al. | |
| 2013/0034686 A1 | 2/2013 | Mitsuno | |
| 2013/0137328 A1 | 5/2013 | Mitsuno | |
| 2013/0226123 A1 | 8/2013 | Kudo et al. | |

FOREIGN PATENT DOCUMENTS

| | | |
|---|---|---|
| EP | 1362568 | 11/2003 |
| EP | 1371379 A1 | 12/2003 |
| EP | 1990033 A1 | 11/2008 |
| EP | 2036521 | 3/2009 |
| EP | 2433602 | 3/2012 |
| GB | 2262235 | 6/1993 |
| JP | S57-17081 B2 | 4/1982 |
| JP | S64-34365 A | 2/1989 |
| JP | S64-56051 | 3/1989 |
| JP | H01-158954 | 6/1989 |
| JP | H02-152920 | 6/1990 |
| JP | H02-229255 A | 9/1990 |
| JP | H05-154176 | 6/1993 |
| JP | H06-5614 | 1/1994 |
| JP | H06-502104 | 3/1994 |
| JP | H07-84697 B2 | 9/1995 |
| JP | H08-510665 | 11/1996 |
| JP | H08-322879 | 12/1996 |
| JP | H10-95810 | 4/1998 |
| JP | H10-510743 | 10/1998 |
| JP | H11-512643 | 11/1999 |
| JP | 2000-510376 | 8/2000 |
| JP | 3091283 | 9/2000 |
| JP | 2000-512886 | 10/2000 |
| JP | 2001-095845 | 4/2001 |
| JP | 2001-129019 | 5/2001 |
| JP | 2001-328191 A | 11/2001 |
| JP | 2002-508693 | 3/2002 |
| JP | 3262172 | 3/2002 |
| JP | 2002-528174 | 9/2002 |
| JP | 2002-537904 | 11/2002 |
| JP | 2003-024372 | 1/2003 |
| JP | 2003-052750 | 2/2003 |
| JP | 2003-192563 A | 7/2003 |
| JP | 2004-500908 | 1/2004 |
| JP | 2004-049529 | 2/2004 |
| JP | 2004-534089 A | 11/2004 |
| JP | 2005-504591 | 2/2005 |
| JP | 2005-095759 | 4/2005 |
| JP | 2005-193001 | 7/2005 |
| JP | 2005-525134 | 8/2005 |
| JP | 2006-501022 | 1/2006 |
| JP | 2006-510456 | 3/2006 |
| JP | 2006-115996 | 5/2006 |

(56) References Cited

FOREIGN PATENT DOCUMENTS

| | | |
|---|---|---|
| JP | 2006-233405 A | 9/2006 |
| JP | 2006-255051 A | 9/2006 |
| JP | 2006-280526 | 10/2006 |
| JP | 2007-014705 | 1/2007 |
| JP | 2007-509695 | 4/2007 |
| JP | 2008-002034 A | 1/2008 |
| JP | 2008-023311 A | 2/2008 |
| JP | 2008-023365 | 2/2008 |
| JP | 2008-025078 A | 2/2008 |
| JP | 2008-025079 A | 2/2008 |
| JP | 2008-025080 A | 2/2008 |
| JP | 2008-025081 A | 2/2008 |
| JP | 2008-025082 A | 2/2008 |
| JP | 2008-025083 A | 2/2008 |
| JP | 2008-025084 A | 2/2008 |
| JP | 2008-025085 A | 2/2008 |
| JP | 2008-029830 | 2/2008 |
| JP | 2008-503323 | 2/2008 |
| JP | 2008-86504 A | 4/2008 |
| JP | 2008-138340 | 6/2008 |
| JP | 2008-144322 | 6/2008 |
| JP | 2008-529721 | 8/2008 |
| JP | 2008-229032 | 10/2008 |
| JP | 2008-229033 | 10/2008 |
| JP | 2008-237569 | 10/2008 |
| JP | 2008-264084 | 11/2008 |
| JP | 2008-266813 | 11/2008 |
| JP | 2008-541943 | 11/2008 |
| JP | 2008-307179 A | 12/2008 |
| JP | 2009-005767 A | 1/2009 |
| JP | 2009-030218 A | 2/2009 |
| JP | 2009-201878 | 9/2009 |
| JP | 2009-531121 A | 9/2009 |
| JP | 2009-268559 A | 11/2009 |
| JP | 2009-297048 | 12/2009 |
| JP | 2010-088822 | 4/2010 |
| JP | 2010-518918 A | 6/2010 |
| JP | 2010-148708 | 7/2010 |
| JP | 2010-526629 | 8/2010 |
| JP | 2010-533535 A | 10/2010 |
| JP | 2010-279568 | 12/2010 |
| JP | 2010-285735 A | 12/2010 |
| JP | 2011-038211 A | 2/2011 |
| JP | 2011-067484 | 4/2011 |
| JP | 2011-072650 | 4/2011 |
| JP | 2011-74500 A | 4/2011 |
| JP | 2011-074515 A | 4/2011 |
| JP | 2011-080178 A | 4/2011 |
| JP | 2011-510801 A | 4/2011 |
| JP | 2011-104001 | 6/2011 |
| JP | 2011-104059 | 6/2011 |
| JP | 2011-110122 A | 6/2011 |
| JP | 2011-120696 | 6/2011 |
| JP | 4693847 | 6/2011 |
| JP | WO 2011065247 A1 * | 6/2011 ......... A61F 13/51104 |
| JP | 2011-226010 | 11/2011 |
| JP | 2011-226011 | 11/2011 |
| JP | 2012-050626 | 3/2012 |
| JP | 5122007 | 1/2013 |
| WO | 93/01781 | 2/1993 |
| WO | 94/27539 | 12/1994 |
| WO | 96/19173 | 6/1996 |
| WO | 98/55158 | 12/1998 |
| WO | 99/00093 | 1/1999 |
| WO | 99/29274 | 6/1999 |
| WO | 00/24351 | 5/2000 |
| WO | 01/45757 | 6/2001 |
| WO | 03/004070 A1 | 1/2003 |
| WO | 03/017900 | 3/2003 |
| WO | 03/028776 | 4/2003 |
| WO | 2004/030713 | 4/2004 |
| WO | 2004/058119 | 7/2004 |
| WO | 2005/044164 | 5/2005 |
| WO | 2006/009996 | 1/2006 |
| WO | 2006-130646 | 12/2006 |
| WO | 2007/113778 A2 | 10/2007 |
| WO | 2008/072675 | 6/2008 |
| WO | 2008/101163 A2 | 8/2008 |
| WO | 2008/139425 | 11/2008 |
| WO | 2008/149771 | 12/2008 |
| WO | 2009/013660 A2 | 1/2009 |
| WO | 2009102837 A2 | 8/2009 |
| WO | 2012/133724 | 10/2012 |

OTHER PUBLICATIONS

Written Opinion mailed Jul. 3, 2012 in corresponding International Application No. PCT/JP2012/058499.
International Search Report mailed Jul. 3, 2012 in corresponding International Application No. PCT/JP2012/058499.
Reply to Written Opinion dated Jan. 30, 2013, corresponds to International Application No. PCT/JP2012/058499.
International Search Report mailed Jul. 17, 2012 in corresponding International Application No. PCT/JP2012/061505.
International Search Report mailed Mar. 19, 2013 in corresponding International Application No. PCT/JP2012/082087.
International Search Report mailed Mar. 12, 2013 in corresponding International Application No. PCT/JP2012/082104.
International Search Report mailed May 21, 2014 in corresponding International Application No. PCT/JP2013/054796.
International Search Report mailed Jan. 8, 2013 in corresponding International Application No. PCT/JP2012/075583.
International Search Report mailed Jul. 2, 2013 in corresponding International Application No. PCT/JP2013/058860.
International Search Report mailed Jul. 2, 2013 in corresponding International Application No. PCT/JP2013/058861.
International Search Report mailed Jul. 2, 2013 in corresponding International Application No. PCT/JP2013/058862.
International Search Report mailed Jun. 18, 2013 in corresponding International Application No. PCT/JP2013/058855.
International Search Report mailed Mar. 26, 2013 in corresponding International Application No. PCT/JP2012/082977.
International Search Report mailed May 14, 2013 in corresponding International Application No. PCT/JP2013/058836.
International Search Report mailed May 21, 2013 in corresponding International Application No. PCT/JP2013/058859.
International Search Report in corresponding PCT Application No. PCT/JP2013/054382 dated Mar. 19, 2013, 1 page.

* cited by examiner

200 μm (a)

|─── 50μm ───|

(b)

|─── 50μm ───|

ABSORBENT ARTICLE

CROSS-REFERENCES TO RELATED APPLICATIONS

The present application is National Phase of International Application Number PCT/JP2013/054382 filed Feb. 21, 2013 and claims the priority of Japanese patent Application No. 2012-044354 filed Feb. 29, 2012.

TECHNICAL FIELD

The present disclosure relates to an absorbent article.

BACKGROUND ART

As the basic performance of absorbent articles, such as sanitary napkins and panty liners has continued to improve with technological development over many years, leakage after absorption of excreta, such as menstrual blood has become a less frequent occurrence than in the past, and research is currently ongoing with the aim of achieving even higher performance, including a feel similar to underwear, and smoothness of the top sheet even after absorption of excreta, such as menstrual blood.

Menstrual blood during menstruation, in particular, can also contain components of the endometrium which are highly viscous, and the top sheet preferably remains smooth and stick-free even after absorption of such highly viscous menstrual blood. Highly viscous menstrual blood usually remains on the top sheet in the form of masses, generally leaving the user with a visually unpleasant image, and therefore from this viewpoint as well it is preferred for no highly viscous menstrual blood to remain on the top sheet.

In addition, the menstrual blood discharge during menstruation is not constant, but discharge of menstrual blood varies depending on the period after the start of menstruation, at times involving a large amount of menstrual blood discharge at once, and at other times a small amount of menstrual blood discharge at once. Menstrual blood is not constantly discharged during menstruation, and there are even periods without discharge of menstrual blood.

Consequently, there are periods when a large amount of menstrual blood reaches the top sheet side at once, periods when small amounts of menstrual blood reach it at once, and periods when no menstrual blood reaches it at all, and preferably the menstrual blood migrates into the absorbent body without remaining on the top sheet, regardless of the amount of menstrual blood.

Absorbent articles are known in the technical field which are coated with lotion compositions.

For example, PTL 1 discloses an absorbent article having a polypropylene glycol material-containing lotion composition situated on the inner surface of the top sheet (the clothing side surface), the inner surface of the back sheet (the body side surface), and on the base material between the inner surface of the top sheet and the inner surface of the back sheet.

Also, PTL 2 discloses an absorbent article wherein a polypropylene glycol material-containing lotion composition is applied on the outer surface of the top sheet (body side surface).

CITATION LIST

Patent Literature

PTL 1 Japanese Unexamined Patent Publication No. 2010-518918

PTL 2 Japanese Unexamined Patent Publication No. 2011-510801

SUMMARY OF INVENTION

Technical Problem

However, the inventions described in PTL 1 and 2 are not designed so that menstrual blood migrates into the absorbent body without remaining on the top sheet regardless of the amount of menstrual blood, and nothing is mentioned regarding the relationship between the lotion composition and the top sheet, and especially the shape of the top sheet.

It is therefore an object of the present disclosure to provide an absorbent article without a sticky feel on the top sheet and with a smooth top sheet, not only when a large amount of menstrual blood has been absorbed, but even when a small amount of menstrual blood has been absorbed.

Solution to Problems

As a result of diligent research directed toward solving the problems described above, the present inventors have discovered an absorbent article comprising a liquid-permeable top sheet, a liquid-impermeable back sheet and an absorbent body between the liquid-permeable top sheet and liquid-impermeable back sheet, wherein the liquid-permeable top sheet has an uneven structure comprising at least one projection and at least one recess on a skin contact surface, the liquid-permeable top sheet contains a blood slipping agent having a kinematic viscosity of 0.01 to 80 $mm^2/s$ at 40° C., a water holding percentage of 0.01 to 4.0 mass %, and a weight-average molecular weight of less than 1,000, on at least the projection in an excretory opening contact region.

Advantageous Effects of Invention

The absorbent article of the present disclosure has no sticky feel on the top sheet and has a smooth top sheet, not only when a large amount of menstrual blood has been absorbed, but even when a small amount of menstrual blood has been absorbed.

DESCRIPTION OF EMBODIMENTS

Figure 1:
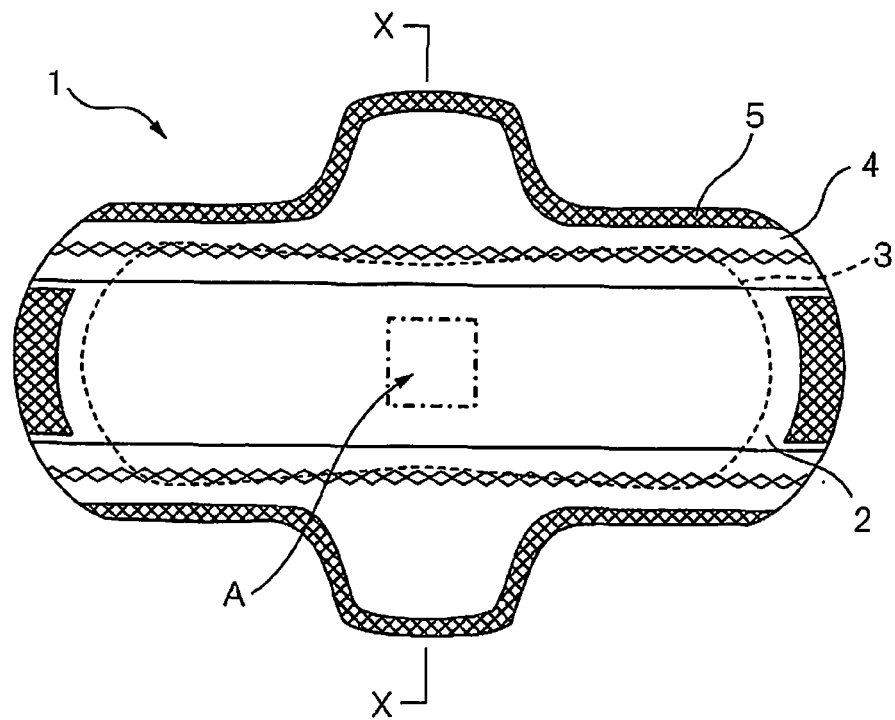
FIG. 1 is a front view of a sanitary napkin, as an embodiment of an absorbent article of the invention.

The absorbent article of the present disclosure will now be explained in detail.

[Liquid-Permeable Top Sheet]

In the absorbent article of the present disclosure, the liquid-permeable top sheet has an uneven structure comprising at least one projection and at least one recess on the skin contact surface. The mechanism of the present disclosure will be described below, but in order for the menstrual blood that has reached the projection to migrate to the recess and subsequently into the absorbent body in the absorbent article of the present disclosure, the difference between the height of the projection and the height of the recess is preferably constant.

The height of the projection is preferably about 0.1 to about 15.0 mm higher, more preferably about 0.5 to about 5.0 mm higher and even more preferably about 0.5 to about 2.0 mm higher than the height of the recess. If the difference in heights is less than about 0.1 mm, it will be difficult for menstrual blood to migrate from the projection to the recess and subsequently into the absorbent body, while if the difference in heights is greater than about 15.0 mm, the projection will tend to be easily collapsable during wear.

The heights of the projection and the recess can be measured using a high precision laser displacement meter, such as an LJ-G Series two-dimensional laser displacement gauge (Model: LJ-G030) by Keyence Corp.

Examples of top sheets having uneven structures include those in which the liquid-permeable top sheet has a ridge-furrow structure comprising a plurality of ridges and a plurality of furrows on the skin contact surface, such as the nonwoven fabrics described in Japanese Examined Patent Publication HEI No. 7-84697, Japanese Unexamined Patent Publication HEI No. 2-229255, Japanese Unexamined Patent Publication No. 2001-328191, Japanese Unexamined Patent Publication No. 2008-002034, No. 2008-023311, No. 2008-025078, No. 2008-025085, No. 2008-307179, No. 2009-030218, No. 2010-285735, No. 2011-038211, No. 2011-074515 and No. 2011-080178, and the porous films described in Japanese Unexamined Patent Publication SHO No. 64-34365 and Japanese Examined Patent Publication SHO No. 57-17081.

For an embodiment in which the uneven structure is a ridge-furrow structure, the heights of the ridges are preferably about 0.1 to about 15.0 mm higher, more preferably about 0.5 to about 5.0 mm higher and even more preferably about 0.5 to about 2.0 mm higher than the heights of the furrows. The pitch of the ridges is preferably about 1.5 to about 17 mm, more preferably about 2.0 to about 12 mm and even more preferably about 3 to about 8 mm. This is so that menstrual blood will slip down from the projection to the recess and then rapidly migrate into the absorbent body.

The liquid-permeable top sheet may have embossed sections formed by embossing at least the liquid-permeable top sheet. For example, the liquid-permeable top sheet may have embossed sections formed by embossing the liquid-permeable top sheet and the absorbent body, and for an embodiment in which the absorbent article of the present disclosure includes a second sheet, the liquid-permeable top sheet may have embossed sections formed by embossing the liquid-permeable top sheet, the second sheet and the absorbent body. If the top sheet has embossed sections, the blood slipping agent will slip down from the projection to the recess, together with menstrual blood, and menstrual blood will subsequently be able to rapidly migrate into the absorbent body.

[Blood Slipping Agent]

For the absorbent article of the present disclosure, the liquid-permeable top sheet contains, at least in the projection, a blood slipping agent having kinematic viscosity of about 0.01 to about 80 mm$^2$/s at 40° C., a water holding percentage of about 0.05 to about 4.0 mass %, and a weight-average molecular weight of less than about 1,000.

The blood slipping agent has, at 40° C., a kinematic viscosity of about 0 to about 80 mm$^2$/s, preferably a kinematic viscosity of about 1 to about 70 mm$^2$/s, more preferably a kinematic viscosity of about 3 to about 60 mm$^2$/s, even more preferably a kinematic viscosity of about 5 to about 50 mm$^2$/s, and yet more preferably a kinematic viscosity of about 7 to about 45 mm$^2$/s.

The kinematic viscosity tends to be higher with a) a larger molecular weight of the blood slipping agent, b) a higher percentage of polar groups, such as carbonyl bonds (—CO—), ether bonds (—O—), carboxyl groups (—COOH) and hydroxyl groups (—OH), and c) a larger IOB.

In order to have a kinematic viscosity of about 0 to about 80 mm$^2$/s at 40° C., the melting point of the blood slipping agent is preferably 45° C. or less. This is because the kinematic viscosity will tend to be higher if the blood slipping agent contains crystals at 40° C.

As used herein, the "kinematic viscosity at 40° C." may be referred to simply as "kinematic viscosity".

The significance of the kinematic viscosity of the blood slipping agent will be explained below, but a kinematic viscosity exceeding about 80 mm$^2$/s will tend to result in high viscosity of the blood slipping agent, such that it will not as easily slip down from the projection to the recess together with menstrual blood that has reached the skin contact surface of the top sheet, and subsequently migrate into the absorbent body.

The kinematic viscosity can be measured according to JIS K 2283:2000, "5. Kinematic Viscosity Test Method", using a Cannon-Fenske reverse-flow viscometer, at a testing temperature of 40° C.

The blood slipping agent has a water holding percentage of about 0.01 to about 4.0 mass %, preferably it has a water holding percentage of about 0.02 to about 3.5 mass %, more preferably it has a water holding percentage of about 0.03 to about 3.0 mass %, even more preferably it has a water holding percentage of about 0.04 to about 2.5 mass %, and yet more preferably it has a water holding percentage of about 0.05 to about 2.0 mass %.

As used herein, "water holding percentage" means the percentage of water that can be held by a substance, and it may be measured in the following manner.

(1) A test tube, a rubber stopper, the substance to be measured and deionized water are allowed to stand for a day and a night in a thermostatic chamber at 40° C.

(2) Into the 20 mL test tube in the thermostatic chamber there are charged 5.0 g of the substance to be measured and 5.0 g of deionized water.

(3) The mouth of the test tube is sealed with the rubber stopper in the thermostatic chamber, and it is rotated once and allowed to stand for 5 minutes.

(4) A 3.0 g portion of the layer of the substance to be measured (usually the upper layer) is sampled into a glass dish with a diameter of 90 mm (weight: $W_0$), in the thermostatic chamber.

(5) The dish is heated at 105° C. for 3 hours in an oven to evaporate off the moisture, and the weight of each dish is measured (weight: $W_1$).

(6) The water holding percentage is calculated by the following formula.

$$\text{Water holding percentage (\%)} = 100 \times (W_0 - W_1)/3.0$$

The measurement is conducted three times, and the average value is recorded.

The significance of the water holding percentage of the blood slipping agent will be explained below, but a low water holding percentage will tend to lower the affinity between the blood slipping agent and menstrual blood, thus impeding its migration into the absorbent body together with menstrual blood that has reached the skin contact surface of the top sheet. If the water holding percentage is high, on the other hand, the affinity between menstrual blood and the blood slipping agent will become very high, similar to a surfactant, and absorbed menstrual blood will tend to remain on the skin contact surface of the top sheet, resulting in more red coloration of the skin contact surface of the top sheet.

The water holding percentage tends to be a larger value with a) a smaller molecular weight of the blood slipping agent, and b) a higher percentage of polar groups, such as carbonyl bonds (—CO—), ether bonds (—O—), carboxyl groups (—COOH) and hydroxyl groups (—OH). This is because the blood slipping agent has greater hydrophilicity. The water holding percentage will tend to have a larger value with a greater IOB, i.e. with a higher inorganic value or with a lower organic value. This is because the blood slipping agent will have greater hydrophilicity.

The significance of the kinematic viscosity and water holding percentage of the blood slipping agent will now be explained.

FIG. 1 is a front view of a sanitary napkin, as an embodiment of an absorbent article of the invention, as viewed from the skin contact side. The sanitary napkin 1 shown in FIG. 1 has its forward direction facing left in the drawing. The sanitary napkin 1 shown in FIG. 1 has a liquid-permeable top sheet 2, an absorbent body 3, and a liquid-impermeable back sheet (not shown). The sanitary napkin 1 in FIG. 1 is also shown as having a side sheet 4 and embossed sections 5.

In the sanitary napkin 1 shown in FIG. 1, the top sheet has a plurality of ridges and a plurality of furrows on the skin contact surface, extending in the lengthwise direction of the absorbent article, and the ridges and furrows may be omitted as appropriate. In the sanitary napkin 1 shown in FIG. 1, the ridges and furrows are disposed in an alternating fashion in the widthwise direction of the absorbent article. The side sheet 4 and embossed section 5 are shown for the sanitary napkin 1 illustrated in FIG. 1, but another embodiment of the absorbent article of the present disclosure is an absorbent article without a side sheet and embossed sections.

Figure 2:
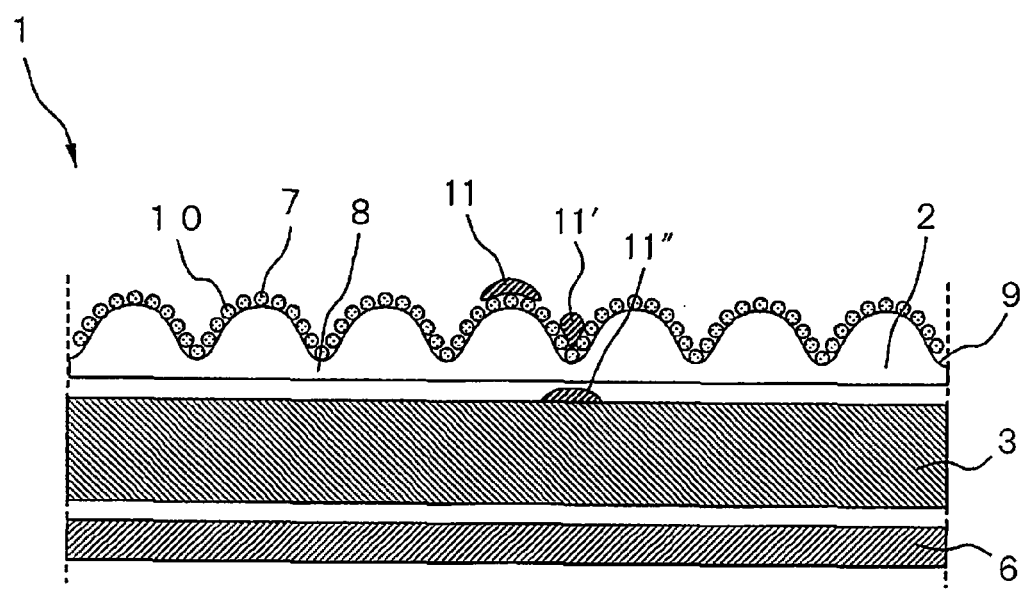
FIG. 2 is a cross-sectional view of section A of the sanitary napkin 1 shown in FIG. 1, along X-X.

FIG. 2 is a cross-sectional view of section A of the sanitary napkin 1 shown in FIG. 1, along X-X. The sanitary napkin 1 shown in FIG. 2 comprises a liquid-permeable top sheet 2, a liquid-impermeable back sheet 6, and an absorbent body 3 between the liquid-permeable top sheet 2 and liquid-impermeable back sheet 6. In FIG. 2, the top sheet 2 has projections 7 and recesses 8 on the skin contact surface 9, and a blood slipping agent 10 coated on the skin contact surface 9 of the top sheet 2. In FIG. 2, the blood slipping agent 10 is shown as droplets on the skin contact surface 9 of the top sheet 2 for convenience, but according to the absorbent article of the present disclosure, the form and distribution of the blood slipping agent is not limited to that shown in the drawing.

As shown in FIG. 2, highly viscous menstrual blood 11 that has reached the projections 7 on the skin contact surface 9 of the top sheet 2 contacts with the blood slipping agent 10 that is present at least on the projections 7. The blood slipping agent 10 having the prescribed water holding percentage and kinematic viscosity slips down into the recesses 8 together with the menstrual blood 11, becoming menstrual blood 11', and then the menstrual blood 11' passes mainly through the recesses 8, reaching the absorbent body 3 to become menstrual blood 11", and is rapidly absorbed into the absorbent body 3.

More specifically, since the blood slipping agent 10 with a kinematic viscosity of about 0.01 to about 80 mm$^2$/s at 40° C. has very low viscosity near the body temperature of the wearer and has a constant affinity with the menstrual blood 11, it slips down from the projections 7 to the recesses 8 together with the menstrual blood 11, and utilizing the energy during slipping, the menstrual blood 11' is able to pass through the recesses 8 of the top sheet 2 to rapidly migrate into the absorbent body 3. Also, since the blood slipping agent 10 present in the projections 7 has a water holding percentage of about 0.01 to about 4.0 mass %, presumably it has no affinity with the hydrophilic component (blood plasma, etc.) in the menstrual blood 11, and therefore the menstrual blood 11 does not easily remain on the top sheet.

When the menstrual blood 11 is a large amount of menstrual blood, the menstrual blood 11 easily migrates into the absorbent body 3, even when the kinetic energy of the menstrual blood 11 itself is high and the kinematic viscosity of the blood slipping agent 10 is relatively high so that it does not easily slip down together with the menstrual blood 11, or when the water holding percentage value is relatively high so that affinity with the hydrophilic components of the menstrual blood 11 is high, or when the weight-average molecular weight value is relatively high so that it does not easily slip down together with the menstrual blood 11, or when the skin contact surface of the top sheet does not have an uneven structure.

When the menstrual blood 11 is a small amount of menstrual blood, on the other hand, the kinetic energy of the menstrual blood 11 is low, and menstrual blood that has reached the skin contact surface 9 of the top sheet 2 tends to easily pool in such cases. Consequently, the prescribed blood slipping agent slips down from the projections 7 into the recesses 8 together with the menstrual blood 11, and the menstrual blood 11' is drawn into the top sheet 2 and then drawn into the absorbent body 3, so that the menstrual blood can rapidly migrate into the absorbent body.

The blood slipping agent has a weight-average molecular weight of less than about 1,000, and preferably a weight-average molecular weight of less than about 900. This is because, if the weight-average molecular weight is about 1,000 or higher, tack may result in the blood slipping agent itself, tending to create a feeling of unpleasantness for the wearer. If the weight-average molecular weight increases, the viscosity of the blood slipping agent will tend to increase, and it will therefore be difficult to lower the viscosity of the blood slipping agent by heating to a viscosity suitable for coating, and as a result, the blood slipping agent may need to be diluted with a solvent.

The blood slipping agent preferably has a weight-average molecular weight of about 100 or greater, and more preferably it has a weight-average molecular weight of about 200 or greater. This is because if the weight-average molecular weight is low, the vapor pressure of the blood slipping agent may be increased, gasification may occur during storage and the amount may be reduced, often leading to problems, such as odor during wear.

In addition, as used herein, "weight-average molecular weight" includes the concept of a polydisperse compound (for example, a compound produced by stepwise polymerization, an ester formed from a plurality of fatty acids and a plurality of aliphatic monohydric alcohols), and a simple compound (for example, an ester formed from one fatty acid and one aliphatic monohydric alcohol), and in a system comprising $N_i$ molecules with molecular weight $M_i$ (i=1, or i=1, 2 . . . ), it refers to $M_w$ determined by the following formula.

$$M_w = \Sigma N_i M_i^2 / \Sigma N_i M_i$$

As used herein, the weight-average molecular weights are the values measured by gel permeation chromatography (GPC), based on polystyrene.

The GPC measuring conditions may be the following, for example.

Device: Lachrom Elite high-speed liquid chromatogram by Hitachi High-Technologies Corp.

Columns: SHODEX KF-801, KF-803 and KF-804, by Showa Denko K.K.

Eluent: THF

Flow rate: 1.0 mL/min

Driving volume: 100 µL

Detection: RI (differential refractometer)

The weight-average molecular weights listed in the examples of the present specification were measured under the conditions described below.

The blood slipping agent can have an IOB of about 0.00 to about 0.60.

The IOB (Inorganic Organic Balance) is an indicator of the hydrophilic-lipophilic balance, and as used herein, it is the value calculated by the following formula by Oda et al.:

IOB=inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725.

The organic values and inorganic values of major groups, according to Fujita, are summarized in Table 1 below.

TABLE 1

| Group | Inorganic value | Organic value |
|---|---|---|
| —COOH | 150 | 0 |
| —OH | 100 | 0 |
| —O—CO—O— | 80 | 0 |
| —CO— | 65 | 0 |
| —COOR | 60 | 0 |
| —O— | 20 | 0 |
| Triple bond | 3 | 0 |
| Double bond | 2 | 0 |
| $CH_2$ | 0 | 20 |
| iso-branch | 0 | −10 |
| tert-branch | 0 | −20 |
| Light metal (salt) | ≥500 | 0 |
| Heavy metal (salt), amine, $NH_3$ salt | ≥400 | 0 |

For example, in the case of an ester of tetradecanoic acid which has 14 carbon atoms and dodecyl alcohol which has 12 carbon atoms, the organic value is 520 ($CH_2$, 20×26) and the inorganic value is 60 (—COOR, 60×1), and therefore IOB=0.12.

The IOB of the blood slipping agent is preferably between about 0.00 and 0.60, more preferably between about 0.00 and 0.50, even more preferably between about 0.00 and 0.40 and most preferably between about 0.00 and 0.30. If the IOB is within this range, it will be easier to meet the aforementioned conditions for the water-holding capacity and kinematic viscosity.

The blood slipping agent preferably has a melting point of 45° C. or less. If the blood slipping agent has a melting point of 45° C. or less, the blood slipping agent will more easily exhibit a kinematic viscosity in the aforementioned range.

As used herein, the term "melting point" refers to the peak top temperature for the endothermic peak during conversion from solid to liquid, upon measurement with a differential scanning calorimetry analyzer at a temperature-elevating rate of 10° C./min. The melting point may be measured using a Model DSC-60 DSC measuring apparatus by Shimadzu Corp., for example.

If the blood slipping agent has a melting point of about 45° C. or less, it may be either liquid or solid at room temperature (25° C.), or in other words, the melting point may be either about 25° C. or higher or below about 25° C., and for example, it may have a melting point of about −5° C. or about −20° C. The reason for a melting point of about 45° C. or less for the blood slipping agent will be explained below.

The blood slipping agent does not have a lower limit for the melting point, but the vapor pressure is preferably low. The vapor pressure of the blood slipping agent is preferably about 0-200 Pa, more preferably about 0-100 Pa, even more preferably about 0-10 Pa, even more preferably about 0-1 Pa, and even more preferably about 0.0-0.1 Pa at 25° C. (1 atmosphere).

Considering that the absorbent article of this disclosure is to be used in contact with the human body, the vapor pressure is preferably about 0-700 Pa, more preferably about 0-100 Pa, even more preferably about 0-10 Pa, even more preferably about 0-1 Pa, and even more preferably 0.0-0.1 Pa, at 40° C. (1 atmosphere). If the vapor pressure is high, gasification may occur during storage and the amount of blood slipping agent may be reduced, and as a consequence problems, such as odor during wear, may be created.

The melting point of the blood slipping agent may be selected depending on the weather or duration of wear. For example, in regions with a mean atmospheric temperature of about 10° C. or less, using a blood slipping agent with a melting point of about 10° C. or less may help the blood slipping agent function after excretion of menstrual blood, even if it has been cooled by the ambient temperature.

Also, when the absorbent article is to be used for a prolonged period of time, the melting point of the blood slipping agent is preferably at the high end of the range of about 45° C. or less. This is so that the blood slipping agent will not be easily affected by sweat or friction during wearing, and will not easily become biased even during prolonged wearing.

In the technical field, the skin contact surfaces of top sheets are coated with surfactants in order to alter the surface tension of menstrual blood and promote rapid absorption of menstrual blood. However, the top sheet coated with the surfactant has very high affinity for the hydrophilic components (blood plasma, etc.) in menstrual blood, and acts to attract them, tending to cause menstrual blood instead to remain on the top sheet. The blood slipping agent, unlike conventionally known surfactants, has low affinity with menstrual blood and therefore does not cause residue of menstrual blood on the top sheet and allows rapid migration into the absorbent body.

Preferably, the blood slipping agent is selected from the group consisting of following items (i)-(iii), and any combination thereof:

(i) a hydrocarbon;

(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting for a hydrogen of the hydrocarbon moiety.

As used herein, "hydrocarbon" refers to a compound composed of carbon and hydrogen, and it may be a chain hydrocarbon, such as a paraffinic hydrocarbon (containing no double bond or triple bond, also referred to as alkane), an olefin-based hydrocarbon (containing one double bond, also referred to as alkene), an acetylene-based hydrocarbon (containing one triple bond, also referred to as alkyne), or a hydrocarbon comprising two or more bonds selected from the group consisting of double bonds and triple bonds, and cyclic hydrocarbon, such as aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include linear hydrocarbons and branched hydrocarbons.

When two or more oxy groups (—O—) are inserted in the compounds of (ii) and (iii) above, the oxy groups (—O—) are not adjacent each other. Thus, compounds (ii) and (iii) do not include compounds with continuous oxy groups (i.e., peroxides).

In the compounds of (iii), compounds in which at least one hydrogen on the hydrocarbon moiety is substituted with a hydroxyl group (—OH) are preferred over compounds in which at least one hydrogen on the hydrocarbon moiety is substituted with a carboxyl group (—COOH). This is because the carboxyl groups bond with metals and the like in menstrual blood, increasing the water holding percentage of the blood slipping agent, which may sometimes exceed the prescribed range. The same is true from the viewpoint of the IOB as well. As shown in Table 1, the carboxyl groups bond with metals and the like in menstrual blood, drastically increasing the inorganic value from 150 to 400 or greater, and therefore a blood slipping agent with carboxyl groups can increase the IOB value to more than about 0.60 during use.

More preferably, the blood slipping agent is selected from the group consisting of following items (i')-(iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting for a hydrogen on the hydrocarbon moiety.

When 2 or more same or different bonds are inserted in the compound of (ii') or (iii'), i.e., when 2 or more same or different bonds selected from the group consisting carbonyl bonds (—CO—), ester bonds (—COO—), carbonate bonds (—OCOO—) and ether bonds (—O—) are inserted, the bonds are not adjacent to each other, and at least one carbon atom lies between each of the bonds.

The blood slipping agent has more preferably about 1.8 or less carbonyl bonds (—CO—), about 2 or less ester bonds (—COO—), about 1.5 or less carbonate bonds (—OCOO—), about 6 or less ether bonds (—O—), about 0.8 or less carboxyl groups (—COOH) and/or about 1.2 or less hydroxyl groups (—OH), per 10 carbon atoms in the hydrocarbon moiety.

Even more preferably, the blood slipping agent is selected from the group consisting of following items (A)-(F), and any combination thereof:

(A) an ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety;

(B) an ether of (B1) a compound having a chain hydrocarbon moiety and 2-4 hydroxyl groups substituting for hydrogens on the chain hydrocarbon moiety, and (B2) a compound having a chain hydrocarbon moiety and 1 hydroxyl group substituting for a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting for hydrogens on the chain hydrocarbon moiety, and (C2) a compound having a chain hydrocarbon moiety and 1 hydroxyl group substituting for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy $C_3$-$C_6$ alkylene glycol, or ester or ether thereof; and (F) a chain hydrocarbon.

The blood slipping agent in accordance with (A) to (F) will now be described in detail.

[(A) Ester of (A1) A Compound Having a Chain Hydrocarbon Moiety and 2-4 Hydroxyl Groups Substituting for Hydrogens on the Chain Hydrocarbon Moiety, and (A2) a Compound Having a Chain Hydrocarbon Moiety and 1 Carboxyl Group Substituting for a Hydrogen on the Chain Hydrocarbon Moiety]

In the (A) ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety (hereunder also referred to as "compound (A)"), it is not necessary for all of the hydroxyl groups to be esterified so long as the kinematic viscosity, water holding percentage and weight-average molecular weight are within the aforementioned ranges.

Examples of (A1) a compound having a chain hydrocarbon moiety and 2-4 hydroxyl groups substituting for hydrogens on the chain hydrocarbon moiety (hereunder also referred to as "compound (A1)") include chain hydrocarbon tetraols, such as alkanetetraols, including pentaerythritol, chain hydrocarbon triols, such as alkanetriols, including glycerins, and chain hydrocarbon diols, such as alkanediols, including glycols.

Examples of (A2) a compound having a chain hydrocarbon moiety and 1 carboxyl group substituting for a hydrogen on the chain hydrocarbon moiety include compounds in which one hydrogen on the hydrocarbon is substituted with one carboxyl group (—COOH), such as fatty acids.

Examples for compound (A) include ($a_1$) an ester of a chain hydrocarbon tetraol and at least one fatty acid, ($a_2$) an ester of a chain hydrocarbon triol and at least one fatty acid, and ($a_3$) an ester of a chain hydrocarbon diol and at least one fatty acids.

[($a_1$) Esters of a Chain Hydrocarbon Tetraol and at Least One Fatty Acid]

Examples of an ester of a chain hydrocarbon tetraol and at least one fatty acid include tetraesters of pentaerythritol and fatty acids, represented by the following formula (1):

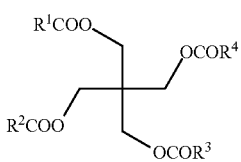

triesters of pentaerythritol and fatty acids, represented by the following formula (2):

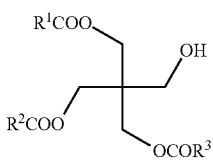

diesters of pentaerythritol and fatty acids, represented by the following formula (3):

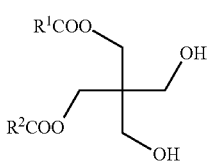

and monoesters of pentaerythritol and fatty acids, represented by the following formula (4).

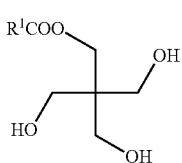

In the formulas, $R^1$-$R^4$ each represent a chain hydrocarbon.

The fatty acids consisting of the esters of pentaerythritol and fatty acids ($R^1$COOH, $R^2$COOH, $R^3$COOH, and $R^4$COOH) are not particularly restricted so long as the pentaerythritol and fatty acid esters satisfy the conditions for the kinematic viscosity, water holding percentage and weight-average molecular weight, and for example, there may be mentioned saturated fatty acids, such as a $C_2$-$C_{30}$ saturated fatty acids, including acetic acid ($C_2$) ($C_2$ representing the number of carbons, corresponding to the number of carbons of each of $R^1$C, $R^2$C, $R^3$C or $R^4$C, same hereunder), propanoic acid ($C_3$), butanoic acid ($C_4$) and isomers thereof, such as 2-methylpropanoic acid ($C_4$), pentanoic acid ($C_5$) and isomers thereof, such as 2-methylbutanoic acid ($C_5$) and 2,2-dimethylpropanoic acid ($C_5$), hexanoic acid ($C_6$), heptanoic acid ($C_7$), octanoic acid ($C_8$) and isomers thereof, such as 2-ethylhexanoic acid ($C_8$), nonanoic acid ($C_9$), decanoic acid ($C_{10}$), dodecanoic acid ($C_{12}$), tetradecanoic acid ($C_{14}$), hexadecanoic acid ($C_{16}$), heptadecanoic acid ($C_{17}$), octadecanoic acid ($C_{18}$), eicosanoic acid ($C_{20}$), docosanoic acid ($C_{22}$), tetracosanoic acid ($C_{24}$), hexacosanoic acid ($C_{26}$), octacosanoic acid ($C_{28}$), triacontanoic acid ($C_{30}$), as well as isomers thereof which are not described above.

The fatty acid may also be an unsaturated fatty acid. Examples of unsaturated fatty acids include $C_2$-$C_{20}$ unsaturated fatty acids, such as monounsaturated fatty acids including crotonic acid ($C_4$), myristoleic acid ($C_{14}$), palmitoleic acid ($C_{16}$), oleic acid ($C_{18}$), elaidic acid ($C_{18}$), vaccenic acid ($C_{18}$), gadoleic acid ($C_{20}$) and eicosenoic acid ($C_{20}$), di-unsaturated fatty acids including linolic acid ($C_{18}$) and eicosadienoic acid ($C_{20}$), tri-unsaturated fatty acids including linolenic acids, such as α-linolenic acid ($C_{18}$) and γ-linolenic acid ($C_{18}$), pinolenic acid ($C_{18}$), eleostearic acids, such as α-eleostearic acid ($C_{18}$) and β-eleostearic acid ($C_{18}$), Mead acid ($C_{20}$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), and partial hydrogen adducts of the foregoing.

Considering the potential for degradation by oxidation and the like, the ester of pentaerythritol and a fatty acid is preferably an ester of pentaerythritol and a fatty acid, which is derived from a saturated fatty acid, i.e., an ester of pentaerythritol and a saturated fatty acid.

Also, from the viewpoint of lowering the water holding percentage, the ester of pentaerythritol and a fatty acid is preferably a diester, triester or tetraester, more preferably a triester or tetraester, and even more preferably a tetraester.

From the viewpoint of the IOB being from about 0.00 to about 0.60, in a tetraester of pentaerythritol and a fatty acid, the total number of carbons of the fatty acid composing the tetraester of the pentaerythritol and fatty acid, i.e. the total number of carbons of the $R^1$C, $R^2$C, $R^3$C and $R^4$C portions in formula (1), is preferably about 15 (the IOB is 0.60 when the total number of carbon atoms is 15).

Examples of tetraesters of pentaerythritol and fatty acids include tetraesters of pentaerythritol with hexanoic acid ($C_6$), heptanoic acid ($C_7$), octanoic acid ($C_8$), such as 2-ethylhexanoic acid ($C_8$), nonanoic acid ($C_9$), decanoic acid ($C_{10}$) and/or dodecanoic acid ($C_{12}$).

From the viewpoint of the IOB being from about 0.00 to about 0.60, in a triester of pentaerythritol and a fatty acid, the total number of carbons of the fatty acid composing the triester of the pentaerythritol and fatty acid, i.e. the total number of carbons of the $R^1C$, $R^2C$ and $R^3C$ portions in formula (2), is preferably about 19 or greater (the IOB is 0.58 when the number of carbon atoms is 19).

From the viewpoint of the IOB being from about 0.00 to about 0.60, in a diester of pentaerythritol and a fatty acid, the total number of carbons of the fatty acid composing the diester of the pentaerythritol and fatty acid, i.e. the total number of carbons of the $R^1C$ and $R^2C$ portion in formula (3), is preferably about 22 or greater (the IOB is 0.59 when the number of carbon atoms is 22).

From the viewpoint of the IOB being from about 0.00 to about 0.60, in a monoester of pentaerythritol and a fatty acid, the total number of carbons of the fatty acid composing the monoester of the pentaerythritol and fatty acid, i.e. the number of carbons of the $R^1C$ portion in formula (4), is preferably about 25 or greater (the IOB is 0.60 when the number of carbon atoms is 25).

The effects of double bonds, triple bonds, iso-branches and tert-branches are not considered in this calculation of the IOB (same hereunder).

Commercial products which are esters of pentaerythritol and fatty acids include UNISTAR H-408BRS and H-2408BRS-22 (mixed product) (both products of NOF Corp.).

[($a_2$) Ester of a Chain Hydrocarbon Triol and at Least One Fatty Acid]

Examples of esters of a chain hydrocarbon triol and at least one fatty acid include triesters of glycerin and fatty acids, represented by formula (5):

diesters of glycerin and fatty acids, represented by the following formula (6):

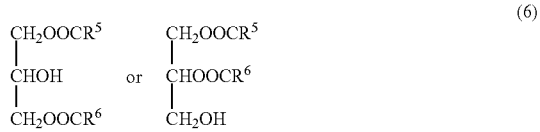

and monoesters of glycerin and fatty acids, represented by the following formula (7):

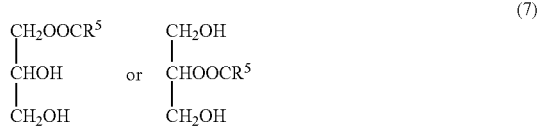

wherein $R^5$-$R^7$ each represent a chain hydrocarbon.

The fatty acid consisting of the ester of glycerin and a fatty acid ($R^5COOH$, $R^6COOH$ and $R^7COOH$) is not particularly restricted so long as the ester of glycerin and a fatty acid satisfies the conditions for the kinematic viscosity, water holding percentage and weight-average molecular weight, and for example, there may be mentioned the fatty acids mentioned for the "($a_1$) Ester of a chain hydrocarbon tetraol and at least one fatty acid", namely saturated fatty acids and unsaturated fatty acids, and in consideration of the potential for degradation by oxidation and the like, the ester is preferably a glycerin and fatty acid ester, which is derived from a saturated fatty acid, i.e., an ester of glycerin and a saturated fatty acid.

Also, from the viewpoint of lowering the water holding percentage and result in greater hydrophobicity, the ester of glycerin and a fatty acid is preferably a diester or triester, and more preferably a triester.

A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or more different fatty acids, and mixtures of the foregoing.

Examples of triesters of glycerin and 2 or more fatty acids include triesters of glycerin with octanoic acid ($C_8$) and decanoic acid ($C_{10}$), triesters of glycerin with octanoic acid ($C_8$), decanoic acid ($C_{10}$) and dodecanoic acid ($C_{12}$), and triesters of glycerin with octanoic acid ($C_8$), decanoic acid ($C_{10}$), dodecanoic acid (C12), tetradecanoic acid ($C_{14}$), hexadecanoic acid ($C_{16}$) and octadecanoic acid ($C_{18}$).

In order to obtain a melting point of about 45° C. or less, preferred triesters of glycerin and fatty acids are those with about 40 or less as the total number of carbons of the fatty acid consisting of the triester of glycerin and the fatty acid, i.e., the total number of carbons of the $R^5C$, $R^6C$ and $R^7C$ sections in formula (5).

From the viewpoint of the IOB being from about 0.00 to about 0.60, in a triester of glycerin and a fatty acid, the total number of carbons of the fatty acid composing the triester of the glycerin and fatty acid, i.e. the total number of carbons of the $R^5C$, $R^6C$ and $R^7C$ portions in formula (5), is preferably about 12 or greater (the IOB is 0.60 when the total number of carbon atoms is 12).

Triesters of glycerin and fatty acids, being aliphatic and therefore potential constituent components of the human body, are preferred from the viewpoint of safety.

Commercial products of triesters of glycerin and fatty acids include tri-coconut fatty acid glycerides, NA36, PANACET 800, PANACET 800B and PANACET 810S, and tri-C2L oil fatty acid glycerides and tri-CL oil fatty acid glycerides (all products of NOF Corp.).

A diester of glycerin and a fatty acid is also known as a diglyceride, and examples include diesters of glycerin and decanoic acid ($C_{10}$), diesters of glycerin and dodecanoic acid ($C_{12}$), diesters of glycerin and hexadecanoic acid ($C_{16}$), diesters of glycerin and 2 or more different fatty acids, and mixtures of the foregoing.

From the viewpoint of the IOB being from about 0.00 to about 0.60, in a diester of glycerin and a fatty acid, the total number of carbons of the fatty acid composing the diester of the glycerin and fatty acid, i.e. the total number of carbons of the $R^5C$ and $R^6C$ portions in formula (6), is preferably about 16 or greater (the IOB is 0.58 when the total number of carbon atoms is 16).

Monoesters of glycerin and fatty acids are also known as monoglycerides, and examples include glycerin and octadecanoic acid ($C_{18}$) monoester, and glycerin and docosanoic acid ($C_{22}$) monoester.

In a monoester of glycerin and a fatty acid, the IOB is 0.59 if the total number of carbons of the fatty acid consisting the monoester of the glycerin and fatty acid, i.e. the number of carbons of the $R^5C$ portion in formula (7), is 19. Thus, when the number of carbons of the fatty acid consisting the monoester of the glycerin and fatty acid is approximately 19 or greater, the IOB satisfies the condition of being about 0.00 to 0.60.

From the viewpoint of the IOB being from about 0.00 to about 0.60, in a monoester of glycerin and a fatty acid, the total number of carbons of the fatty acid composing the monoester of the glycerin and fatty acid, i.e. the number of carbons of the $R^5C$ portion in formula (7), is preferably about 19 or greater (the IOB is 0.59 when the number of carbon atoms is 19).

[($a_3$) Ester of a Chain Hydrocarbon Diol and at Least One Fatty Acid]

Examples of an ester of a chain hydrocarbon diol and at least one fatty acid include monoesters and diesters of fatty acids with $C_2$-$C_6$ chain hydrocarbon diols, such as $C_2$-$C_6$ glycols, including ethylene glycol, propylene glycol, butylene glycol, pentylene glycol and hexylene glycol.

Specifically, examples of an ester of a chain hydrocarbon diol and at least one fatty acid include diesters of $C_2$-$C_6$ glycols and fatty acids, represented by the following formula (8):

$$R^8COOC_kH_{2k}OCOR^9 \qquad (8)$$

wherein k represents an integer of 2-6, and $R^8$ and $R^9$ each represent a chain hydrocarbon,
and monoesters of $C_2$-$C_6$ glycols and fatty acids, represented by the following formula (9):

$$R^9COOC_kH_{2k}OH \qquad (9)$$

wherein k represents an integer of 2-6, and $R^8$ is a chain hydrocarbon.

The fatty acid to be esterified in an ester of a $C_2$-$C_6$ glycol and a fatty acid (corresponding to $R^8COOH$ and $R^9COOH$ in formula (8) and formula (9)) is not particularly restricted so long as the ester of the $C_2$-$C_6$ glycol and fatty acid satisfies the conditions for the kinematic viscosity, water holding percentage and weight-average molecular weight, and for example, there may be mentioned the fatty acids mentioned above for the "($a_1$) Ester of a chain hydrocarbon tetraol and at least one fatty acid", namely saturated fatty acids and unsaturated fatty acids, and in consideration of the potential for degradation by oxidation and the like, it is preferably a saturated fatty acid.

From the viewpoint of the IOB being from about 0.00 to about 0.60, in a diester of butylene glycol represented by formula (8) (k=4) and a fatty acid, the total number of carbons of the $R^8C$ and $R^9C$ portions is preferably about 6 or greater (the IOB is 0.60 when the total number of carbon atoms is 6).

From the viewpoint of the IOB being from about 0.00 to about 0.60, in a monoester of ethylene glycol represented by formula (9) (k=2) and a fatty acid, the number of carbons of the $R^8C$ portion is preferably about 12 or greater (the IOB is 0.57 when the number of carbon atoms is 12).

Considering the potential for degradation by oxidation and the like, the ester of the $C_2$-$C_6$ glycol and fatty acid is preferably a $C_2$-$C_6$ glycol and fatty acid ester derived from a saturated fatty acid, or in other words, an ester of a $C_2$-$C_6$ glycol and a saturated fatty acid.

Also, from the viewpoint of lowering the water holding percentage, the ester of the $C_2$-$C_6$ glycol and fatty acid is preferably a glycol and fatty acid ester derived from a glycol with a greater number of carbons, such as an ester of a glycol and a fatty acid derived from butylene glycol, pentylene glycol or hexylene glycol.

Also, from the viewpoint of lowering the water holding percentage, the ester of a $C_2$-$C_6$ glycol and fatty acid is preferably a diester.

Examples of commercial products of esters of $C_2$-$C_6$ glycols and fatty acids include COMPOL BL and COMPOL BS (both products of NOF Corp.).

[(B) Ether of (B1) a Compound Having a Chain Hydrocarbon Moiety and 2-4 Hydroxyl Groups Substituting for Hydrogens on the Chain Hydrocarbon Moiety and (B2) a Compound Having a Chain Hydrocarbon Moiety and 1 Hydroxyl Group Substituting for a Hydrogen on the Chain Hydrocarbon Moiety]

In the (B) ether of (B1) a compound having a chain hydrocarbon moiety and 2-4 hydroxyl groups substituting for hydrogens on the chain hydrocarbon moiety and (B2) a compound having a chain hydrocarbon moiety and 1 hydroxyl group substituting for a hydrogen on the chain hydrocarbon moiety (hereunder also referred to as "compound (B)"), it is not necessary for all of the hydroxyl groups to be etherified so long as the kinematic viscosity, water holding percentage and weight-average molecular weight are within the aforementioned ranges.

Examples of (B1) a compound having a chain hydrocarbon moiety and 2-4 hydroxyl groups substituting for hydrogens on the chain hydrocarbon moiety (hereunder also referred to as "compound (B1)") include those mentioned for "compound (A)" as compound (A1), such as pentaerythritol, glycerin and glycol.

Examples of (B2) a compound having a chain hydrocarbon moiety and 1 hydroxyl group substituting for a hydrogen on the chain hydrocarbon moiety (hereunder also referred to as "compound (B2)") include compounds wherein 1 hydrogen on the hydrocarbon is substituted with 1 hydroxyl group (—OH), such as aliphatic monohydric alcohols, including saturated aliphatic monohydric alcohols and unsaturated aliphatic monohydric alcohols.

Examples of saturated aliphatic monohydric alcohols include $C_1$-$C_{20}$ saturated aliphatic monohydric alcohols, such as methyl alcohol ($C_1$) ($C_1$ representing the number of carbon atoms, same hereunder), ethyl alcohol ($C_2$), propyl alcohol ($C_3$) and isomers thereof, including isopropyl alcohol ($C_3$), butyl alcohol ($C_4$) and isomers thereof, including sec-butyl alcohol ($C_4$) and tert-butyl alcohol (C4), pentyl alcohol ($C_5$), hexyl alcohol ($C_6$), heptyl alcohol ($C_7$), octyl alcohol ($C_8$) and isomers thereof, including 2-ethylhexyl alcohol ($C_8$), nonyl alcohol ($C_9$), decyl alcohol ($C_{10}$), dodecyl alcohol ($C_{12}$), tetradecyl alcohol ($C_{14}$), hexadecyl alcohol ($C_{16}$), heptadecyl alcohol ($C_{17}$), octadecyl alcohol ($C_{18}$) and eicosyl alcohol ($C_{20}$), as well as their isomers other than those mentioned.

Unsaturated aliphatic monohydric alcohols include those wherein 1° C.—C single bond of a saturated aliphatic monohydric alcohol mentioned above is replaced with a C═C double bond, such as oleyl alcohol, and for example, such alcohols are commercially available by New Japan Chemical Co., Ltd. as the RIKACOL Series and UNJECOL Series.

Examples for compound (B) include ($b_1$) an ether of a chain hydrocarbon tetraol and at least one aliphatic monohydric alcohol, such as monoethers, diethers, triethers and tetraethers, preferably diethers, triethers and tetraethers, more preferably triethers and tetraethers and even more preferably tetraethers, ($b_2$) an ether of a chain hydrocarbon triol and at least one aliphatic monohydric alcohol, such as monoethers, diethers and triethers, preferably diethers and triethers and more preferably triethers, and ($b_3$) an ether of a chain hydrocarbon diol and at least one aliphatic monohydric alcohol, such as monoethers and diethers, and preferably diethers.

Examples of an ether of a chain hydrocarbon tetraol and at least one aliphatic monohydric alcohol include tetraethers, triethers, diethers and monoethers of pentaerythritol and aliphatic monohydric alcohols, represented by the following formulas (10)-(13):

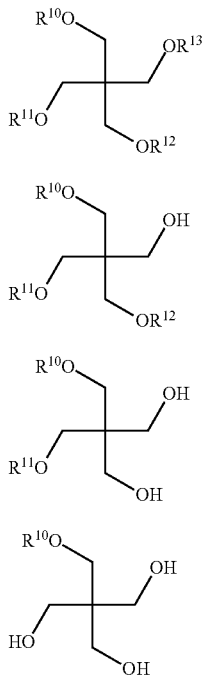

wherein $R^{10}$-$R^{13}$ each represent a chain hydrocarbon.

Examples of an ether of a chain hydrocarbon triol and at least one aliphatic monohydric alcohol include triethers, diethers and monoethers of glycerin and aliphatic monohydric alcohols, represented by the following formulas (14)-(16):

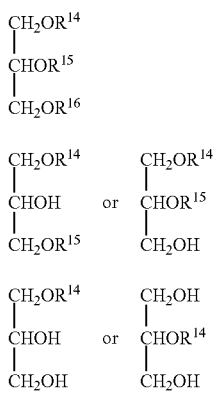

wherein $R^{14}$-$R^{16}$ each represent a chain hydrocarbon.

Examples of an ether of a chain hydrocarbon diol and at least one aliphatic monohydric alcohol include diethers of $C_2$-$C_6$ glycols and aliphatic monohydric alcohols, represented by the following formula (17):

$$R^{17}OC_nH_{2n}OR^{18} \quad (17)$$

wherein n is an integer of 2-6, and $R^{17}$ and $R^{18}$ are each a chain hydrocarbon, and monoethers of $C_2$-$C_6$ glycols and aliphatic monohydric alcohols, represented by the following formula (18):

$$R^{17}OC_nH_{2n}OH \quad (18)$$

wherein n is an integer of 2-6, and $R^{17}$ is a chain hydrocarbon.

From the viewpoint of the IOB being between about 0.00 and about 0.60, in a tetraether of pentaerythritol and an aliphatic monohydric alcohol, the total number of carbon atoms of the aliphatic monohydric alcohol composing the tetraether of pentaerythritol and the aliphatic monohydric alcohol, i.e. the total number of carbon atoms of the $R^{10}$, $R^{11}$, $R^{12}$ and $R^{13}$ portions in formula (10), is preferably about 4 or greater (the IOB is 0.44 when the total number of carbon atoms is 4).

From the viewpoint of the IOB being between about 0.00 and about 0.60, in a triether of pentaerythritol and an aliphatic monohydric alcohol, the total number of carbon atoms of the aliphatic monohydric alcohol composing the triether of pentaerythritol and the aliphatic monohydric alcohol, i.e. the total number of carbon atoms of the $R^{10}$, $R^{11}$ and $R^{12}$ portions in formula (11), is preferably about 9 or greater (the IOB is 0.57 when the total number of carbon atoms is 9).

From the viewpoint of the IOB being between about 0.00 and about 0.60, in a diether of pentaerythritol and an aliphatic monohydric alcohol, the total number of carbon atoms of the aliphatic monohydric alcohol composing the diether of pentaerythritol and the aliphatic monohydric alcohol, i.e. the total number of carbon atoms of the $R^{10}$ and $R^{11}$ portions in formula (12), is preferably about 15 or greater (the IOB is 0.60 when the total number of carbon atoms is 15).

From the viewpoint of the IOB being between about 0.00 and about 0.60, in a monoether of pentaerythritol and an aliphatic monohydric alcohol, the number of carbon atoms of the aliphatic monohydric alcohol composing the monoether of pentaerythritol and the aliphatic monohydric alcohol, i.e. the number of carbon atoms of the $R^{10}$ portion in formula (13), is preferably about 22 or greater (the IOB is 0.59 when the number of carbon atoms is 22).

From the viewpoint of the IOB being between about 0.00 and about 0.60, in a triether of glycerin and an aliphatic monohydric alcohol, the total number of carbon atoms of the aliphatic monohydric alcohol composing the triether of glycerin and the aliphatic monohydric alcohol, i.e. the total number of carbon atoms of the $R^{14}$, $R^{15}$ and $R^{16}$ portions in formula (14), is preferably about 3 or greater (the IOB is 0.50 when the total number of carbon atoms is 3).

From the viewpoint of the IOB being between about 0.00 and about 0.60, in a diether of glycerin and an aliphatic monohydric alcohol, the total number of carbon atoms of the aliphatic monohydric alcohol composing the diether of glycerin and the aliphatic monohydric alcohol, i.e. the total number of carbon atoms of the $R^{14}$ and $R'5$ portions in formula (15), is preferably about 9 or greater (the IOB is 0.58 when the total number of carbon atoms is 9).

From the viewpoint of the IOB being between about 0.00 and about 0.60, in a monoether of glycerin and an aliphatic monohydric alcohol, the number of carbon atoms of the aliphatic monohydric alcohol composing the monoether of glycerin and the aliphatic monohydric alcohol, i.e. the number of carbon atoms of the $R^{14}$ portion in formula (16), is preferably 16 or greater (the IOB is 0.58 when the number of carbon atoms is 16).

From the viewpoint of the IOB being from about 0.00 to about 0.60, in a diether of butylene glycol represented by formula (17) (n=4) and an aliphatic monohydric alcohol, the total number of carbon atoms of the $R^{17}$ and $R^{18}$ portions is preferably about 2 or greater (the IOB is 0.33 when the total number of carbon atoms is 2).

From the viewpoint of the IOB being from about 0.00 to about 0.60, in a monoether of ethylene glycol represented by formula (18) (n=2) and an aliphatic monohydric alcohol, the number of carbon atoms of the $R'^{7}$ portion is preferably about 8 or greater (the IOB is 0.60 when the number of carbon atoms is 8).

Compound (B) may be produced by dehydrating condensation of compound (B1) and compound (B2) in the presence of an acid catalyst.

[(C) Ester of (C1) a Carboxylic Acid, Hydroxy Acid, Alkoxy Acid or Oxoacid Comprising a Chain Hydrocarbon Moiety and 2-4 Carboxyl Groups Substituting for Hydrogens on the Chain Hydrocarbon Moiety and (C2) a Compound Having a Chain Hydrocarbon Moiety and 1 Hydroxyl Group Substituting for a Hydrogen on the Chain Hydrocarbon Moiety]

In the (C) ester of (C1) a carboxylic acid, hydroxy acid, alkoxy acid or oxoacid comprising a chain hydrocarbon moiety and 2-4 carboxyl groups substituting for hydrogens on the chain hydrocarbon moiety and (C2) a compound having a chain hydrocarbon moiety and 1 hydroxyl group substituting for a hydrogen on the chain hydrocarbon moiety (hereunder also referred to as "compound (C)"), it is not necessary for all of the carboxyl groups to be esterified so long as the kinematic viscosity, water holding percentage and weight-average molecular weight are within the aforementioned ranges.

Examples of (C1) a carboxylic acid, hydroxy acid, alkoxy acid or oxoacid comprising a chain hydrocarbon moiety and 2-4 carboxyl groups substituting for hydrogens on the chain hydrocarbon moiety (hereunder also referred to as "compound (C1)") include chain hydrocarbon carboxylic acids with 2-4 carboxyl groups, such as chain hydrocarbon dicarboxylic acids including alkanedicarboxylic acids, such as ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, including alkanetricarboxylic acids, such as propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, including alkanetetracarboxylic acids, such as butanetetraoic acid, pentanetetraoic acid, hexanetetraoic acid, heptanetetraoic acid, octanetetraoic acid, nonanetetraoic acid and decanetetraoic acid.

Compound (C1) includes chain hydrocarbon hydroxy acids with 2-4 carboxyl groups, such as malic acid, tartaric acid, citric acid and isocitric acid, chain hydrocarbon alkoxy acids with 2-4 carboxyl groups, such as O-acetylcitric acid, and chain hydrocarbon oxoacids with 2-4 carboxyl groups.

(C2) Compound having a chain hydrocarbon moiety and 1 hydroxyl group substituting for a hydrogen on the chain hydrocarbon moiety includes those mentioned for "compound (B)", such as aliphatic monohydric alcohols.

Compound (C) may be ($c_1$) an ester, for example a monoester, diester, triester, preferably a diester, triester or tetraester, more preferably a triester or tetraester and even more preferably a tetraester, of a chain hydrocarbon tetracarboxylic acid, hydroxy acid, alkoxy acid or oxoacid with 4 carboxyl groups, and at least one aliphatic monohydric alcohol, ($c_2$) an ester, for example, a monoester, diester or triester, preferably a diester or triester and more preferably a triester, of a chain hydrocarbon tricarboxylic acid, hydroxy acid, alkoxy acid or oxoacid with 3 carboxyl groups, and at least one aliphatic monohydric alcohol, or ($c_3$) an ester, for example, a monoester or diester, and preferably a diester, of a chain hydrocarbon dicarboxylic acid, hydroxy acid, alkoxy acid or oxoacid with 2 carboxyl groups, and at least one aliphatic monohydric alcohol.

Examples for compound (C) include dioctyl adipate, diisostearyl malate, tributyl citrate and tributyl 0-acetylcitrate, of which commercially available products exist.

[(D) Compound Having a Chain Hydrocarbon Moiety and One Bond Selected from the Group Consisting of an Ether Bond (—O—), Carbonyl Bond (—CO—), Ester Bond (—COO—) and Carbonate Bond (—OCOO—) Inserted Between a C—C Single Bond of the Chain Hydrocarbon Moiety]

The (D) compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety (hereunder also referred to as "compound (D)") may be ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, or ($d_4$) a dialkyl carbonate.

[($d_1$) Ether of an Aliphatic Monohydric Alcohol and an Aliphatic Monohydric Alcohol]

Ethers of an aliphatic monohydric alcohol and an aliphatic monohydric alcohol include compounds having the following formula (19):

$$R^{19}OR^{20} \tag{19}$$

wherein $R^{19}$ and $R^{20}$ each represent a chain hydrocarbon.

The aliphatic monohydric alcohol consisting of the ether (corresponding to $R^{19}OH$ and $R^{20}OH$ in formula (19)) is not particularly restricted so long as the ether satisfies the conditions for the kinematic viscosity, water holding percentage and weight-average molecular weight, and for example, it may be one of the aliphatic monohydric alcohols mentioned for "compound (B)".

[($d_2$) Dialkyl Ketone]

The dialkyl ketone may be a compound of the following formula (20):

$$R^{21}COR^{22} \tag{20}$$

wherein $R^{21}$ and $R^{22}$ are each an alkyl group.

The dialkyl ketone may be a commercially available product, or it may be obtained by a known method, such as by oxidation of a secondary alcohol with chromic acid or the like.

[($d_3$) Ester of a Fatty Acid and an Aliphatic Monohydric Alcohol]

Examples of esters of a fatty acid and an aliphatic monohydric alcohol include compounds having the following formula (21):

$$R^{23}COOR^{24} \tag{21}$$

wherein $R^{23}$ and $R^{24}$ each represent a chain hydrocarbon.

Examples of fatty acids consisting of these esters (corresponding to $R^{23}COOH$ in formula (21)) include the fatty acids mentioned for the "($a_1$) an ester of a chain hydrocarbon tetraol and at least one fatty acids", and specifically these include saturated fatty acids and unsaturated fatty acids, with saturated fatty acids being preferred in consideration of the potential for degradation by oxidation and the like. The aliphatic monohydric alcohol consisting of the ester (corresponding to $R^{24}OH$ in formula (21)) may be one of the aliphatic monohydric alcohols mentioned for "compound (B)".

Examples of esters of such fatty acids and aliphatic monohydric alcohols include esters of dodecanoic acid ($C_{12}$) and dodecyl alcohol ($C_{12}$) and esters of tetradecanoic acid ($C_{14}$) and dodecyl alcohol ($C_{12}$), and examples of commercial products of esters of such fatty acids and aliphatic monohydric alcohols include ELECTOL WE20 and ELECTOL WE40 (both products of NOF Corp.).

[($d_4$) Dialkyl Carbonate]

The dialkyl carbonate may be a compound of the following formula (22):

$$R^{25}OC(=O)OR^{26} \quad (22)$$

wherein $R^{25}$ and $R^{26}$ are each an alkyl group.

The dialkyl carbonate may be a commercially available product, or it may be synthesized by reaction between phosgene and an alcohol, reaction between formic chloride and an alcohol or alcoholate, or reaction between silver carbonate and an alkyl iodide.

From the viewpoint of the water holding percentage and vapor pressure, the weight-average molecular weight is preferably about 100 or greater and more preferably about 200 or greater, for ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, and ($d_4$) a dialkyl carbonate.

If the total number of carbon atoms is about 8 in a ($d_2$) dialkyl ketone, the melting point will be approximately $-50°$ C. and the vapor pressure will be about 230 Pa at 20° C., in the case of 5-nonanone, for example.

[(E) Polyoxy $C_3$-$C_6$ Alkylene Glycol, or Alkyl Ester or Alkyl Ether Thereof]

The (E) polyoxy $C_3$-$C_6$ alkylene glycol, or alkyl ester or alkyl ether thereof (hereunder also referred to as "compound (E)") may be ($e_1$) a polyoxy $C_3$-$C_6$ alkylene glycol, ($e_2$) an ester of a polyoxy $C_3$-$C_6$ alkylene glycol and at least one fatty acid, or ($e_3$) an ether of a polyoxy $C_3$-$C_6$ alkylene glycol and at least one aliphatic monohydric alcohol. These will now be explained.

[($e_1$) Polyoxy $C_3$-$C_6$ Alkylene Glycol]

Polyoxy $C_3$-$C_6$ alkylene glycols refer to i) one or more homopolymers having a unit selected from the group consisting of oxy $C_3$-$C_6$ alkylene units, such as oxypropylene unit, oxybutylene unit, oxypentylene unit and oxyhexylene unit and having hydroxyl groups at both ends, ii) one or more block copolymers having 2 or more units selected from oxy $C_3$-$C_6$ alkylene units described above and oxyhexylene unit and having hydroxyl groups at both ends, or iii) random copolymers having 2 or more units selected from oxy $C_3$-$C_6$ alkylene units described above and having hydroxyl groups at both ends.

The polyoxy $C_3$-$C_6$ alkylene glycol can be represented by the following formula (23):

$$HO-(C_mH_{2m}O)_n-H \quad (23)$$

wherein m represents an integer of 3-6.

The present inventors have found that with polypropylene glycol (corresponding to a homopolymer of formula (23) where m=3), the condition for the water holding percentage is not satisfied when the weight-average molecular weight is less than about 1,000. Therefore, polypropylene glycol homopolymer is not included in the scope of the blood slipping agent described above, and propylene glycol should be included in the ($e_1$) polyoxy $C_3$-$C_6$ alkylene glycol only as a copolymer or random polymer with another glycol.

Incidentally, investigation by the present inventors suggests that with polyethylene glycol (corresponding to a homopolymer of formula (23) where m=2), the condition for the kinematic viscosity and water holding percentage cannot be satisfied when the weight-average molecular weight is less than about 1,000.

From the viewpoint of the IOB being about 0.00 to about 0.60, when formula (23) is polybutylene glycol (a homopolymer where m=4), for example, preferably n about 7 (when n=7, the IOB is 0.57).

Examples of commercial products of poly $C_3$-$C_6$ alkylene glycols include UNIOL™ PB-500 and PB-700 (all products of NOF Corp.).

[($e_2$) Ester of a Polyoxy $C_3$-$C_6$ Alkylene Glycol and at Least One Fatty Acid]

Examples of an ester of a polyoxy $C_3$-$C_6$ alkylene glycol and at least one fatty acids include the polyoxy $C_3$-$C_6$ alkylene glycols mentioned for "($e_1$) Polyoxy $C_3$-$C_6$ alkylene glycol" in which one or both OH ends have been esterified with fatty acids, i.e. monoesters and diesters.

Examples of fatty acids to be esterified in the ester of a polyoxy $C_3$-$C_6$ alkylene glycol and at least one fatty acid include the fatty acids mentioned for the "($a_1$) Ester of a chain hydrocarbon tetraol and at least one fatty acid", and specifically these include saturated fatty acids and unsaturated fatty acids, with saturated fatty acids being preferred in consideration of the potential for degradation by oxidation and the like.

[($e_3$) Ether of a Polyoxy $C_3$-$C_6$ Alkylene Glycol and at Least One Aliphatic Monohydric Alcohol]

Examples of an ether of a polyoxy $C_3$-$C_6$ alkylene glycols and at least one aliphatic monohydric alcohol include the polyoxy $C_3$-$C_6$ alkylene glycols mentioned for "($e_1$) Polyoxy $C_3$-$C_6$ alkylene glycol" wherein one or both OH ends have been etherified by an aliphatic monohydric alcohol, i.e. monoethers and diethers.

In an ether of a polyoxy $C_3$-$C_6$ alkylene glycol and at least one aliphatic monohydric alcohol, the aliphatic monohydric alcohol to be etherified may be an aliphatic monohydric alcohol among those mentioned for "compound (B)".

[(F) Chain Hydrocarbon]

Examples of chain hydrocarbons include ($f_1$) chain alkanes, such as straight-chain alkanes and branched chain alkanes. Straight-chain alkanes with melting points of about 45° C. or less have up to about 22 carbon atoms, and at a vapor pressure of 1 atmosphere and no greater than about 0.01 Pa at 25° C., the number of carbon atoms is 13 or greater. Branched chain alkanes tend to have lower melting points than chain alkanes, given the same number of carbon atoms. Branched chain alkanes may therefore include those with 22 and more carbon atoms, even with melting points of below about 45° C.

Examples of Commercially Available Hydrocarbon Products Include PARLEAM 6 (NOF Corp.).

The liquid-permeable top sheet may be any one that is commonly used in the art without any particular restrictions, so long as it has an uneven structure comprising at least one projection and at least one recess on the skin contact surface, and for example, it may be a sheet-like material having a structure that allows permeation of liquids, such as a film, woven fabric, nonwoven fabric or the like. The fibers composing such a woven fabric or nonwoven fabric may be natural fibers or chemical fibers, with examples of natural fibers including cellulose, such as ground pulp and cotton, and examples of chemical fibers including regenerated cellulose, such as rayon and fibril rayon, semi-synthetic cellulose, such as acetate and triacetate, thermoplastic hydrophobic chemical fibers, and hydrophilicized thermoplastic hydrophobic chemical fibers.

Examples of thermoplastic hydrophobic chemical fibers include polyethylene (PE), polypropylene (PP) and polyethylene terephthalate (PET) monofilaments, and fibers including PE and PP graft polymers.

Examples of nonwoven fabrics include air-through nonwoven fabrics, spunbond nonwoven fabrics, point bond nonwoven fabrics, spunlace nonwoven fabrics, needle punching nonwoven fabrics and meltblown nonwoven fabrics, as well as combinations thereof (such as SMS and the like).

Liquid-impermeable back sheets include films comprising PE and PP, air-permeable resin films, air-permeable resin films bonded to spunbond or spunlace nonwoven fabrics, and multilayer nonwoven fabrics, such as SMS. In consideration of flexibility of the absorbent article, a low-density polyethylene (LDPE) film with a basis weight of about 15-30 $g/m^2$, for example, is preferred.

According to one embodiment of the absorbent article of the present disclosure, the absorbent article may comprise a second sheet between the liquid-permeable top sheet and the absorbent body. The second sheet may be any of the same examples as for the liquid-permeable top sheet.

The first example of the absorbent body is one having an absorbent core covered with a core wrap.

Examples of components for the absorbent core include hydrophilic fibers, including cellulose, such as ground pulp or cotton, regenerated cellulose, such as rayon or fibril rayon, semi-synthetic cellulose, such as acetate or triacetate, particulate polymers, filamentous polymers, thermoplastic hydrophobic chemical fibers, and hydrophilicized thermoplastic hydrophobic chemical fibers, as well as combinations of the foregoing. The component of the absorbent core may also be a super absorbent polymer, such as granules of a sodium acrylate copolymer or the like.

The core wrap is not particularly restricted so long as it is a substance that is liquid-permeable and with a barrier property that does not allow permeation of the polymer absorber, and it may be a woven fabric or nonwoven fabric, for example. The woven fabric or nonwoven fabric may be made of a natural fiber, chemical fiber, tissue, or the like.

A second example of the absorbent body is one formed from an absorbing sheet or polymer sheet, with a thickness of preferably about 0.3-5.0 mm. The absorbing sheet or polymer sheet may usually be used without any particular restrictions so long as it is one that can be used in an absorbent article, such as a sanitary napkin.

The blood slipping agent may be present at any location in the planar direction of the top sheet, such as across the entire top sheet, or at the center region near the vaginal opening.

As regards the region in the planar direction wherein the liquid-permeable top sheet includes a blood slipping agent, according to one embodiment of the absorbent article of the present disclosure, the liquid-permeable top sheet comprises a blood slipping agent in the excretory opening contact region. According to another embodiment of the present disclosure, the liquid-permeable top sheet also comprises a blood slipping agent in regions other than the excretory opening contact region, in addition to the excretory opening contact region, and for example, it may comprise the blood slipping agent across the entire surface of the top sheet.

Similarly, as regards the region in the planar direction wherein the liquid-permeable top sheet includes a blood slipping agent, according to one embodiment of the absorbent article of the present disclosure, the liquid-permeable top sheet comprises a blood slipping agent on at least the projection of the uneven structure on the skin contact surface. If the blood slipping agent is present on the projection, the blood slipping agent present on the projection will slip down into the recess together with the menstrual blood that has reached the projection, and menstrual blood can then migrate into the absorbent body.

According to another embodiment of the absorbent article of the present disclosure, the liquid-permeable top sheet comprises a blood slipping agent on both the projection and the recess of the uneven structure. If the blood slipping agent is present on both the projection and the recess, the blood slipping agent present on the projection will slip down into the recess together with the menstrual blood that has reached the projection, and then the blood slipping agent present in the recess can cause menstrual blood that has slipped down into the recess to migrate into the absorbent body.

As regards the region in the thickness direction in which the liquid-permeable top sheet includes a blood slipping agent, according to an embodiment of the absorbent article of the present disclosure, the liquid-permeable top sheet comprises a blood slipping agent on the surface of the skin side, i.e. on the skin contact surface. If the blood slipping agent is present on the skin contact surface of the top sheet, menstrual blood that has reached the projection will slip down into the recess and be able to migrate into the absorbent body. According to another embodiment of the absorbent article of the present disclosure, particularly an embodiment in which the liquid-permeable top sheet is a woven fabric or nonwoven fabric, the liquid-permeable top sheet includes a blood slipping agent on the skin contact surface and in the interior between the skin contact surface and the clothing side surface. According to yet another embodiment of the absorbent article of the present disclosure, the liquid-permeable top sheet includes a blood slipping agent over the entire thickness direction, i.e. on the skin contact surface, in the interior between the skin contact surface and the clothing side surface, and on the clothing side surface. If the blood slipping agent is present in the top sheet interior and/or on the clothing side surface, menstrual blood present on the skin contact surface will be able to rapidly migrate into the absorbent body.

When the liquid-permeable top sheet is formed from a nonwoven fabric or woven fabric, the blood slipping agent preferably does not obstruct the voids between the fibers of the nonwoven fabric or woven fabric, and for example, the blood slipping agent may be attached as droplets or particulates on the surface of the nonwoven fabric or woven fabric fibers, or covering the surfaces of the fibers.

On the other hand, when the liquid-permeable top sheet is formed from a porous film, the blood slipping agent preferably does not obstruct the holes in the porous film, and for example, the blood slipping agent may be attached as droplets or particulates on the surface of the porous film. This is because if the blood slipping agent obstructs the holes in the porous film, migration of the absorbed liquid into the absorbent body may be inhibited.

In order for the blood slipping agent to slip down together with the absorbed menstrual blood, it preferably has a large surface area, and a blood slipping agent present as droplets or particulates preferably has a small droplet/particle size.

According to another embodiment of the absorbent article of the present disclosure, the absorbent article has a second sheet comprising a blood slipping agent.

According to yet another embodiment of the absorbent article of the present disclosure, the absorbent article has an absorbent body comprising a blood slipping agent.

In this absorbent article, the top sheet comprises the blood slipping agent at a basis weight in the range of preferably between about 1 and about 30 g/m², more preferably between about 2 and about 20 g/m² and more preferably between about 3 and about 10 g/m². If the basis weight of the blood slipping agent is lower than about 1 g/m², the absorbed menstrual blood will tend to remain in the top sheet, while if the basis weight of the blood slipping agent is greater than 30 g/m², there will tend to be an increase in sticky feel during wear.

When the material to be coated with the blood slipping agent, such as the top sheet, is a nonwoven fabric, woven fabric or porous film made of a synthetic resin, it is preferably subjected to hydrophilicizing treatment by coating the surface with a hydrophilic agent, or by combining it with a synthetic resin or a film. This is because, if the original material is hydrophilic, there will be lipophilic regions due to the blood slipping agent and hydrophilic regions due to the hydrophilic agent sparsely dispersed on the top sheet, which will facilitate slipping down of menstrual blood onto the projection and recess of the top sheet, and its subsequent migration into the absorbent body.

In an embodiment in which the domed section comprises a blood slipping agent, there are no particular restrictions on the method of coating the blood slipping agent, and coating may be accomplished with heating as necessary, using a non-contact coater, such as for example, a spiral coater, curtain coater, spray coater or dip coater, or a contact coater or the like. A non-contact coater is preferred from the viewpoint of uniformly dispersing the droplet or particulate of the blood slipping agent throughout, and from the viewpoint of not causing damage in the material. The blood slipping agent may be coated directly, if it is a liquid at room temperature, or it may be heated to lower the viscosity, and when it is a solid at room temperature, it may be heated to liquefaction and coated through a control seam hot melt adhesive (HMA) gun. By increasing the air pressure of the control seam HMA gun, it is possible to coat the blood slipping agent as fine particulates.

In an embodiment in which the domed section comprises a blood slipping agent, the blood slipping agent may be coated during production of the material for the top sheet and/or second sheet, such as the nonwoven fabric, or it may be coated in the manufacturing line for production of the absorbent article. In an embodiment in which the domed section comprises a blood slipping agent, from the viewpoint of minimizing equipment investment, the blood slipping agent is preferably coated in the manufacturing line for the absorbent article, and in order to prevent shedding of the blood slipping agent which may contaminate the line, the blood slipping agent is preferably coated during a step downstream from the manufacturing line, and specifically, immediately before encapsulation of the product in an individual package.

The blood slipping agent also has an effect as a lubricant. When the top sheet is a nonwoven fabric, therefore, the blood slipping agent can reduce friction between fibers, thereby improving the flexibility of the nonwoven fabric as a whole. When the top sheet is a resin film, the blood slipping agent can reduce friction between the top sheet and the skin.

According to a preferred embodiment of the absorbent article of the present disclosure, the absorbent article is one that is intended for absorption of blood, such as a sanitary napkin or panty liner.

An absorbent article of the present disclosure does not require components, such as emollients and immobilizing agents, unlike in an absorbent article containing a known skin care composition, lotion composition or the like, and the blood slipping agent alone may be applied to the top sheet.

EXAMPLES

The blood slipping agents used for testing are listed below.

[($a_1$) Ester of a Chain Hydrocarbon Tetraols and at Least One Fatty Acid]

UNISTAR H-408BRS, product of NOF Corp.

Pentaerythritol tetra(2-ethylhexanoate), weight-average molecular weight: approximately 640

UNISTAR H-2408BRS-22, product of NOF Corp.

Mixture of pentaerythritol tetra(2-ethylhexanoate) and neopentylglycol di(2-ethylhexanoate) (58:42 as weight ratio), weight-average molecular weight: approximately 520

[($a_2$) Ester of a Chain Hydrocarbon Triols and at Least One Fatty Acid]

Tri-C2L oil fatty acid glyceride, product of NOF Corp.

Glycerin and fatty acid triester with $C_8$ fatty acid:$C_{10}$ fatty acid:$C_{12}$ fatty acid at a mass ratio of about 37:7:56, weight-average molecular weight: approximately 570

Tri-CL oil fatty acid glyceride, product of NOF Corp.

Glycerin and fatty acid triester with $C_8$ fatty acid:$C_{12}$ fatty acid at a mass ratio of about 44:56, weight-average molecular weight: approximately 570

PANACET 810s, product of NOF Corp.

Glycerin and fatty acid triester with $C_8$ fatty acid:$C_n$ fatty acid at a mass ratio of about 85:15, weight-average molecular weight: approximately 480

PANACET 800, product of NOF Corp.

Glycerin and fatty acid triester with octanoic acid ($C_8$) as the entire fatty acid portion, weight-average molecular weight: approximately 470

PANACET 800B, product of NOF Corp.

Glycerin and fatty acid triester with 2-ethylhexanoic acid ($C_8$) as the entire fatty acid portion, weight-average molecular weight: approximately 470

NA36, product of NOF Corp.

Glycerin and fatty acid triester with $C_{16}$ fatty acid:$C_{18}$ fatty acid:$C_{20}$ fatty acid (including both saturated fatty acids and unsaturated fatty acids) at a mass ratio of about 5:92:3, weight-average molecular weight: approximately 880

Tri-coconut fatty acid glyceride, product of NOF Corp.

Glycerin and fatty acid triester with $C_8$ fatty acid:$C_{10}$ fatty acid:$C_{12}$ fatty acid:$C_{14}$ fatty acid:$C_{16}$ fatty acid (including both saturated fatty acids and unsaturated fatty acids) at a mass ratio of about 4:8:60:25:3, weight-average molecular weight: 670

Caprylic acid diglyceride, product of NOF Corp.

Glycerin and fatty acid diester with octanoic acid as the fatty acid, weight-average molecular weight: approximately 340

[($a_3$) Ester of a Chain Hydrocarbon Diol and at Least One Fatty Acid]

UNISTAR H-208BRS, product of NOF Corp.

Neopentyl glycol di(2-ethylhexanoate), weight-average molecular weight: approximately 360

COMPOL BL, product of NOF Corp.

Dodecanoic acid ($C_{12}$) monoester of butylene glycol, weight-average molecular weight: approximately 270

COMPOL BS, product of NOF Corp.

Octadecanoic acid ($C_{18}$) monoester of butylene glycol, weight-average molecular weight: approximately 350

[(C2) Ester of a Chain Hydrocarbon Tricarboxylic Acid, Hydroxy Acid, Alkoxy Acid or Oxoacid with 3 Carboxyl Groups, and at Least One Aliphatic Monohydric Alcohol]

Tributyl O-acetylcitrate, product of Tokyo Kasei Kogyo Co., Ltd.

Weight-average molecular weight: approximately 400

Tributyl citrate, product of Tokyo Kasei Kogyo Co., Ltd.

Weight-average molecular weight: approximately 360

[(c3) Ester of a Chain Hydrocarbon Dicarboxylic Acid, Hydroxy Acid, Alkoxy Acid or Oxoacid with 2 Carboxyl Groups, and at Least One Aliphatic Monohydric Alcohol]

Dioctyl Adipate, product of Wako Pure Chemical Industries, Ltd.

Weight-average molecular weight: approximately 380

[($d_3$) Ester of a Fatty Acid and an Aliphatic Monohydric Alcohol]

ELECTOL WE20, product of NOF Corp.

Ester of dodecanoic acid ($C_{12}$) and dodecyl alcohol ($C_{12}$), weight-average molecular weight: approximately 360

ELECTOL WE40, product of NOF Corp.

Ester of tetradecanoic acid ($C_{14}$) and dodecyl alcohol ($C_{12}$), weight-average molecular weight: approximately 390

[($e_1$) Polyoxy $C_3$-$C_6$ Alkylene Glycol]

UNIOL PB500, Product of NOF Corp.

Polybutylene glycol, weight-average molecular weight: approximately 500

UNIOL PB700, product of NOF Corp.

Polyoxybutylene polyoxypropylene glycol, weight-average molecular weight: approximately 700

[($f_1$) Chain Alkane]

PARLEAM 6, product of NOF Corp.

Branched chain hydrocarbon, produced by copolymerization of liquid isoparaffin, isobutene and n-butene followed by hydrogen addition, polymerization degree: approximately 5-10, weight-average molecular weight: approximately 330

[Other Materials]

NA50, product of NOF Corp.

Glycerin and fatty acid triester obtained by addition of hydrogen to NA36 for reduced proportion of double bonds from unsaturated fatty acid starting material, weight-average molecular weight: approximately 880

(Caprylic acid/capric acid) monoglyceride, product of NOF Corp.

Glycerin and fatty acid monoester, with octanoic acid ($C_8$) and decanoic acid ($C_{10}$) at a mass ratio of about 85:15, weight-average molecular weight: approximately 220

Monomuls 90-L2 lauric acid monoglyceride, product of Cognis Japan

Isopropyl citrate, product of Tokyo Kasei Kogyo Co., Ltd.

Weight-average molecular weight: approximately 230

Diisostearyl malate

Weight-average molecular weight: approximately 640

UNIOL PB1000R, product of NOF Corp.

Polybutylene glycol, weight-average molecular weight: approximately 1,000

UNIOL D-250, product of NOF Corp.

Polypropylene glycol, weight-average molecular weight: approximately 250

UNIOL D-400, product of NOF Corp.

Polypropylene glycol, weight-average molecular weight: approximately 400

UNIOL D-700, product of NOF Corp.

Polypropylene glycol, weight-average molecular weight: approximately 700

UNIOL D-1000, product of NOF Corp.

Polypropylene glycol, weight-average molecular weight: approximately 1,000

UNIOL D-1200, product of NOF Corp.

Polypropylene glycol, weight-average molecular weight: approximately 1,160

UNIOL D-2000, product of NOF Corp.

Polypropylene glycol, weight-average molecular weight: approximately 2,030

UNIOL D-3000, product of NOF Corp.

Polypropylene glycol, weight-average molecular weight: approximately 3,000

UNIOL D-4000, product of NOF Corp.

Polypropylene glycol, weight-average molecular weight: approximately 4,000

PEG1500, product of NOF Corp.

Polyethylene glycol, weight-average molecular weight: approximately 1,500-1,600

WILBRITE cp9, product of NOF Corp.

Polybutylene glycol compound with OH groups at both ends esterified by hexadecanoic acid ($C_{16}$), weight-average molecular weight: approximately 1,150

UNILUBE MS-70K, product of NOF Corp.

Stearyl ether of polypropylene glycol, approximately 15 repeating units, weight-average molecular weight: approximately 1,140

NONION S-6, product of NOF Corp.

Polyoxyethylene monostearate, approximately 7 repeating units, weight-average molecular weight: approximately 880

UNILUBE 5TP-300 KB

Polyoxyethylene polyoxypropylene pentaerythritol ether, produced by addition of 5 mol of ethylene oxide and 65 mol of propylene oxide to 1 mol of pentaerythritol, weight-average molecular weight: 4,130

WILBRITE s753, product of NOF Corp.

Polyoxyethylene polyoxypropylene polyoxybutylene glycerin, weight-average molecular weight: approximately 960

UNIOL TG-330, product of NOF Corp.

Glyceryl ether of polypropylene glycol, approximately 6 repeating units, weight-average molecular weight: approximately 330

UNIOL TG-1000, product of NOF Corp.

Glyceryl ether of polypropylene glycol, approximately 16 repeating units, weight-average molecular weight: approximately 1,000

UNIOL TG-3000, product of NOF Corp.

Glyceryl ether of polypropylene glycol, approximately 16 repeating units, weight-average molecular weight: approximately 3,000

UNIOL TG-4000, product of NOF Corp.

Glyceryl ether of polypropylene glycol, approximately 16 repeating units, weight-average molecular weight: approximately 4,000

UNILUBE DGP-700, product of NOF Corp.

Diglyceryl ether of polypropylene glycol, approximately 9 repeating units, weight-average molecular weight: approximately 700

UNIOX HC60, product of NOF Corp.

Polyoxyethylene hydrogenated castor oil, weight-average molecular weight: approximately 3,570

Vaseline, product of Cognis Japan

Petroleum-derived hydrocarbon, semi-solid

[Instance 1]

[Menstrual Blood Surface Residue Rate A, with Absorption of Large Amount of Blood]

A test was conducted to evaluate the absorption property of a sanitary napkin after one-time absorption of a large amount of blood.

There were prepared a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150 to 450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The top sheet was a top sheet produced by the method described in Japanese Unexamined Patent Publication No. 2008-2034, having a ridge-furrow structure, with a ridge thickness of approximately 1.5 mm and a furrow thickness of approximately 0.4 mm, the pitch of the ridge-furrow structure (ridge width+furrow width) was approximately 4 mm, and open holes were formed in the furrows at an open area of approximately 15%.

UNISTAR H-408BRS (product of NOF Corp., tetraester of pentaerythritol and fatty acid) was selected as the blood slipping agent, and it was coated onto the skin contact surface (ridge-furrow side) of the top sheet from a control seam HMA gun at room temperature, to a basis weight of 5.0 g/m$^2$. With an electron microscope it was confirmed that the H-408BRS was adhering onto the fiber surfaces as fine particulates.

A back sheet, an absorbent body, a second sheet, and a top sheet with the ridge-furrow side facing upward, were stacked in that order to form sanitary napkin No. 1-1.

Sanitary napkins No. 1-2 to No. 1-49 were produced, changing the blood slipping agent from UNISTAR H-408BRS to the ones listed in Table 2. Each blood slipping agent was used directly, when it was liquid at room temperature, or when the blood slipping agent was solid at room temperature it was heated to its melting point of +20° C., and then a control seam HMA gun was used for atomization of the blood slipping agent and coating onto the skin contact surface of the top sheet to a basis weight of about 5 g/m$^2$.

The blood slipping agent was coated onto essentially the entire skin contact surface of the top sheet, and on both the ridges and furrows.

[Test Methods]

After measuring the weight $W_2$ of the top sheet (the weight of the top sheet before the test), an acrylic board with an opened hole (200 mm×100 mm, 125 g, with a 40 mm×10 mm hole opened at the center) was placed on the top sheet, at the center section in the lengthwise direction and widthwise direction of the absorbent article, and 4.0 g of horse EDTA blood at 37±1° C. (obtained by adding ethylenediaminetetraacetic acid (hereunder, "EDTA") to horse blood to prevent coagulation) was dropped through the hole using a pipette.

After dropping the horse EDTA blood, the acrylic board was immediately removed, the top sheet was taken off, the weight $W_3$ (weight of top sheet after the test) was measured and the "surface residue rate A (mass %)" was calculated by the following formula.

Surface residue rate $A(\text{mass \%}) = 100 \times (W_3 - W_2)/4.0$

The tack on the skin contact surface of the top sheet was measured at 35° C., and evaluated on the following scale.

G: No tack
F: Slight tack
P: Tack

Figure 3:
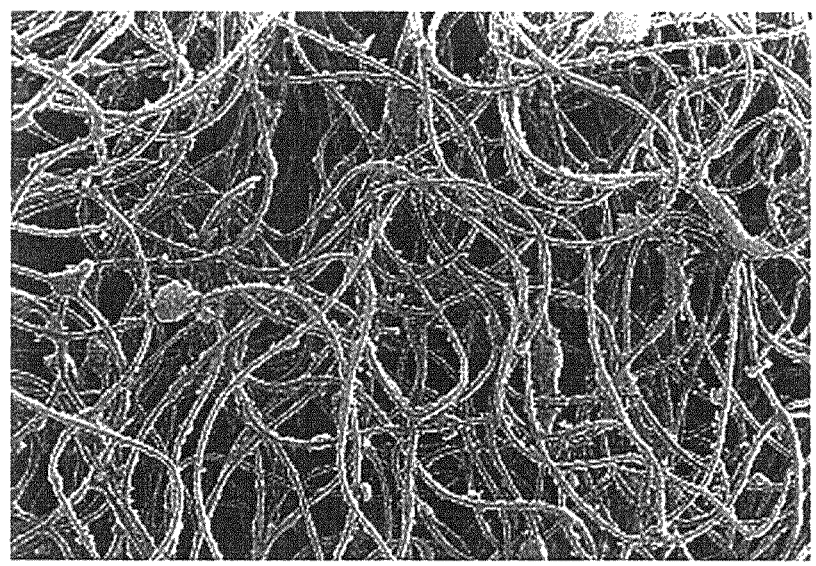
FIG. 3 is an electron micrograph of the skin contact surface of a top sheet in a sanitary napkin wherein the top sheet comprises tri-C2L oil fatty acid glycerides.

The surface residue rate A and tack of each absorbent article, and the properties of each blood slipping agent, are shown below in Table 2. FIG. 3 is an electron micrograph of the skin contact surface of a top sheet in a sanitary napkin wherein the top sheet comprises tri-C2L oil fatty acid glycerides.

TABLE 2

| No. | Blood slipping agent | Kinematic viscosity (mm$^2$/s, 40° C.) | Water holding percentage (mass %) | Weight-average mol. wt. | IOB | Melting point (° C.) | Surface residue rate A (mass %) | Tack |
|---|---|---|---|---|---|---|---|---|
| 1-1 | H-408BRS | 45 | 0.7 | 640 | 0.13 | <−5 | 0.8 | G |
| 1-2 | H-2408BRS-22 | 22 | 0.8 | 520 | 0.18 | <−5 | 0.8 | G |
| 1-3 | Tri-C2L oil fatty acid glyceride | 20 | <1.0 | 570 | 0.27 | 37 | | G |
| 1-4 | Tri-CL oil fatty acid glyceride | 15 | <1.0 | 570 | 0.28 | 38 | | G |
| 1-5 | PANACET 810s | 9 | 0.3 | 480 | 0.32 | −5 | 0.8 | G |
| 1-6 | PANACET 800 | 15 | 0.5 | 470 | 0.33 | −5 | 1.8 | G |
| 1-7 | PANACET 800B | 20 | <1.0 | 470 | 0.33 | −5 | | G |
| 1-8 | NA36 | 40 | <1.0 | 880 | 0.16 | 37 | | G |
| 1-9 | Tri-coconut oil fatty acid glyceride | 25 | <1.0 | 670 | 0.28 | 30 | | G |
| 1-10 | Capric acid diglyceride | 25 | 2.7 | 340 | 0.58 | <45 | 1.0 | G |
| 1-11 | UNISTAR H-208BRS | 8 | 0.7 | 360 | 0.24 | <−5 | 0.5 | G |
| 1-12 | COMPOL BL | 10 | 1.6 | 270 | 0.50 | 2 | 1.3 | G |
| 1-13 | COMPOL BS | 35 | 0.3 | 350 | 0.36 | 37 | 2.5 | G |
| 1-14 | Tributyl O-acetylcitrate | 15 | 0.9 | 400 | 0.60 | <45 | 0.5 | G |
| 1-15 | Tributyl citrate | 12 | 0.6 | 360 | 0.78 | <45 | 1.8 | G |
| 1-16 | Dioctyl adipate | 7 | 0.4 | 380 | 0.27 | <45 | 1.5 | G |
| 1-17 | ELECTOL WE20 | 10 | 0.3 | 360 | 0.13 | 29 | 0.5 | G |
| 1-18 | ELECTOL WE40 | 15 | 0.5 | 390 | 0.12 | 37 | 2.3 | G |
| 1-19 | UNIOL PB500 | 40 | 3.6 | 500 | 0.44 | <45 | 2.5 | G |
| 1-20 | UNIOL PB700 | 50 | 2.3 | 700 | 0.49 | −5 | 1.3 | G |
| 1-21 | PARLEAM 6 | 5 | 0.06 | 330 | 0.00 | −5 | 2.0 | G |
| 1-22 | NA50 | 80<< | —* | 880 | 0.18 | 52 | 4.3 | G |
| 1-23 | (Caprylic acid/Capric acid) monoglyceride | 70 | 4.0<< | 220 | 1.15 | <45 | 5.0 | G |
| 1-24 | 90-L2 Lauric acid monoglyceride | 80<< | 4.0<< | <1,000 | 0.87 | 58 | 5.0 | G |

TABLE 2-continued

| No. | Blood slipping agent | Kinematic viscosity (mm²/s, 40° C.) | Water holding percentage (mass %) | Weight-average mol. wt. | IOB | Melting point (° C.) | Surface residue rate A (mass %) | Tack |
|---|---|---|---|---|---|---|---|---|
| 1-25 | Isopropyl citrate | 120 | 4.0<< | 230 | 1.56 | <45 | 4.8 | F |
| 1-26 | Diisostearyl malate | 450 | 4.0<< | 640 | 0.28 | <45 | 3.3 | F |
| 1-27 | UNIOL PB1000R | 70 | 5.5 | 1,000 | 0.40 | <45 | 2.5 | F |
| 1-28 | UNIOL D-250 | 20 | 4.0<< | 250 | | <45 | 3.8 | G |
| 1-29 | UNIOL D-400 | 30 | 4.0<< | 400 | 0.76 | <45 | 4.8 | G |
| 1-30 | UNIOL D-700 | 50 | 34.6 | 700 | 0.58 | <45 | 4.8 | G |
| 1-31 | UNIOL D-1000 | 70 | 26.7 | 1,000 | 0.51 | <45 | 3.8 | F |
| 1-32 | UNIOL D-1200 | 90 | 16.2 | 1,160 | 0.48 | <45 | 3.0 | F |
| 1-33 | UNIOL D-2000 | 160 | | 2,030 | | <45 | | P |
| 1-34 | UNIOL D-3000 | | 0.6 | 3,000 | 0.39 | <45 | 3.0 | P |
| 1-35 | UNIOL D-4000 | 450 | 0.5 | 4,000 | 0.38 | <45 | 2.5 | P |
| 1-36 | PEG1500 | 120 | 4.0<< | 1,500–1,600 | 0.78 | 40 | 5.5 | P |
| 1-37 | WILBRITE CP9 | 120 | 0.6 | 1,150 | 0.21 | 35 | 6.8 | P |
| 1-38 | UNILUBE MS-70K | 50 | 2.8 | 1,140 | 0.30 | <−10 | 1.5 | F |
| 1-39 | NONION S-6 | 65 | 4.0<< | 880 | 0.44 | 37 | | G |
| 1-40 | UNILUBE 5TP-300KB | 310 | 3.9 | 4,130 | 0.39 | <45 | 2.0 | P |
| 1-41 | WILBRITE s753 | 120 | 27.3 | 960 | 0.67 | −5 | 3.5 | F |
| 1-42 | UNIOL TG-330 | 30 | | 330 | 1.27 | <45 | | G |
| 1-43 | UNIOL TG-1000 | 100 | 21.2 | 1,000 | 0.61 | <45 | 3.5 | G |
| 1-44 | UNIOL TG-3000 | 230 | 4.3 | 3,000 | 0.42 | <45 | 1.0 | P |
| 1-45 | UNIOL TG-4000 | 300 | 2.4 | 4,000 | 0.40 | <45 | 2.0 | P |
| 1-46 | UNILUBE DGP-700 | 200 | 4.0<< | 700 | 0.91 | <0 | 3.5 | F |
| 1-47 | UNIOX HC60 | 1150 | | 3,570 | 0.46 | 33 | | P |
| 1-48 | Vaseline | 80<< | 0.0 | <1,000 | 0.00 | 55 | 4.0 | P |
| 1-49 | None | — | — | — | — | — | 7.5 | G |

*High viscosity, unmeasurable.

With sanitary napkin No. 1-49, which had no blood slipping agent, the surface residue rate A was 7.5 mass %, but with sanitary napkins No. 1-1 to No. 1-21 wherein the kinematic viscosity and water holding percentage were within the prescribed ranges, the surface residue rate A was 2.5 mass % or lower.

With sanitary napkins No. 1-1 to No. 1-21, it was observed that the horse EDTA blood that was dropped onto the ridges of the top sheet slipped down from the ridges into the furrows, and was rapidly absorbed from the furrows into the absorbent body. However, with sanitary napkin No. 1-49 which had no blood slipping agent, the dropped horse EDTA blood did not slip down into the furrows but slowly dripped down into the furrows, most of it remaining on the ridges of the top sheet. Also, with the absorbent articles with high water holding percentage, as with No. 1-30, for example, the horse EDTA blood that was dropped onto the ridges of the top sheet did not slip down into the furrows but slowly dripped while partially remaining on the top sheet, and a portion thereof remained on the ridges.

This suggests that sanitary napkins No. 1-1 to No. 1-21 allow rapid migration of menstrual blood from the top sheet into the absorbent body, when a large amount of menstrual blood has reached the top sheet at once.

Next, several volunteer subjects were asked to wear sanitary napkins Nos. 1-1 to 1-49, and most of the obtained responses indicated that with the sanitary napkins comprising blood slipping agents Nos. 1-1 to 1-21, the top sheets had no sticky feel and the top sheets were smooth, even after absorption of menstrual blood.

[Instance 2]
[Menstrual Blood Surface Residue Rate B, with Absorption of Small Amount of Blood]

A test was conducted to evaluate the absorption property of a sanitary napkin after absorption of a small amount of blood.

There were prepared a top sheet, formed of a hydrophilic agent-treated air-through nonwoven fabric (composite fiber composed of polyester and polyethylene terephthalate, basis weight: 35 g/m²) (hereunder also referred to as "top sheet with ridges-furrows"), a second sheet, formed of an air-through nonwoven fabric (composite fiber composed of polyester and polyethylene terephthalate, basis weight: 30 g/m²), an absorbent body comprising pulp (basis weight: 150 to 450 g/m², increased at the center section), an acrylic super-absorbent polymer (basis weight: 15 g/m²) and tissue as a core wrap, a water-repellent agent-treated side sheet, and a back sheet composed of a polyethylene film.

The top sheet was a top sheet produced by the method described in Japanese Unexamined Patent Publication No. 2008-2034, having a ridge-furrow structure, with a ridge thickness of approximately 1.5 mm and a furrow thickness of approximately 0.4 mm, and the pitch of the ridge-furrow structure (ridge width+furrow width) was approximately 4 mm and open holes were formed in the furrows at an open area of approximately 15%.

UNISTAR H-408BRS (product of NOF Corp., tetraester of pentaerythritol and fatty acid) was selected as the blood slipping agent, and it was coated onto the skin contact surface (ridge-furrow side) of the top sheet from a control seam HMA gun at room temperature, to a basis weight of 5.0 g/m². With an electron microscope it was confirmed that the H-408BRS was adhering onto the fiber surfaces as fine particulates.

A back sheet, an absorbent body, a second sheet, and a top sheet with the ridge-furrow side facing upward, were stacked in that order to form sanitary napkin No. 2-1(i).

A sanitary napkin No. 2-1(ii) was formed in the same manner as the sanitary napkin No. 2-1(i), except that the top sheet was changed to a top sheet formed of a flat hydrophilic agent-treated air-through nonwoven fabric (composite fiber composed of polyester and polyethylene terephthalate, basis weight: 35 g/m²), without a ridge-furrow structure (hereunder also referred to as "flat top sheet").

Sanitary napkins No. 2-2(i) to No. 2-11(i) and No. 2-2(ii) to No. 2-11(ii) were produced, changing the blood slipping agent from UNISTAR H-408BRS to the ones listed in Table 3. Each blood slipping agent was used directly, when it was liquid at room temperature, or when the blood slipping agent was solid at room temperature it was heated to its melting point of +20° C., and then a control seam HMA gun was used for atomization of the blood slipping agent and coating onto the skin contact surface of the top sheet to a basis weight of about 5 g/m².

The blood slipping agent was coated over essentially the entire skin contact surface of the top sheet, and on both the ridges and furrows of the top sheets with a ridge-furrow structure.

[Test Methods]

After measuring the weight $W_4$ of the top sheet (the weight of the top sheet before the test), approximately 0.25 g (2 drops) of horse EDTA blood at 37±1° C. was added dropwise through a pipette, on the top sheet at the center in the lengthwise direction and widthwise direction of the absorbent article. The horse EDTA blood was dropped onto the top parts of the ridges, in the top sheets with ridges-furrows.

At 30 seconds after dropping, the top sheet was taken off, the weight $W_5$ (weight of top sheet after the test) was measured and the "surface residue rate B (mass %)" was calculated by the following formula.

Surface residue rate $B$(mass %)=100×($W_5$−$W_4$)/$W_6$ $W_6$ is the weight of the dropped horse EDTA blood, calculated from the weight of the pipette before and after dropping.

The results are shown in Table 3 below.

TABLE 3

| No. | Blood slipping agent | Surface residue rate B (mass %) | |
|---|---|---|---|
| | | Top sheet with ridge-furrows | Flat top sheet |
| 2-1 | H-408BRS | 4% | 32% |
| 2-2 | PANACET 810S | 8% | 40% |
| 2-3 | Capric acid diglyceride | 8% | 24% |
| 2-4 | COMPOL BL | 4% | 32% |
| 2-5 | Tributyl O-acetylcitrate | 8% | 44% |
| 2-6 | Dioctyl adipate | 8% | 32% |
| 2-7 | ELECTOL WE40 | 8% | 24% |
| 2-8 | UNIOL PB500 | 4% | 68% |
| 2-9 | PARLEAM 6 | 4% | 100% |
| 2-10 | UNIOL D-250 | 16% | 48% |
| 2-11 | None | 28% | 28% |

Table 3 shows that when the blood slipping agent was H-408BRS, PANACET 810S, capric acid diglyceride, COMPOL BL, tributyl 0-acetylcitrate, dioctyl adipate, ELECTOL WE40, UNIOL PB500 or PARLEAM 6, the surface residue rate B of the top sheet with ridges-furrows was low. This suggests that blood slipping agents having the prescribed properties cause rapid migration of small amounts of blood from the ridges to the furrows and into the absorbent body.

Example 3

Viscosity of Blood Containing Blood Slipping Agent

The viscosity of the blood slipping agent-containing blood was measured using a Rheometric Expansion System ARES (Rheometric Scientific, Inc.). After adding 2 mass % of PANACET 810s to horse defibrinated blood, the mixture was gently agitated to form a sample, the sample was placed on a 50 mm-diameter parallel plate, with a gap of 100 μm, and the viscosity was measured at 37±0.5° C. The sample was not subjected to a uniform shear rate due to the parallel plate, but the average shear rate indicated by the device was 10 s⁻¹.

The viscosity of the horse defibrinated blood containing 2 mass % PANACET 810s was 5.9 mPa·s, while the viscosity of the horse defibrinated blood containing no blood slipping agent was 50.4 mPa·s. Thus, the horse defibrinated blood containing 2 mass % PANACET 810s clearly had an approximately 90% lower viscosity than the blood containing no blood slipping agent.

It is known that blood contains components, such as blood cells and has a thixotropic nature, and it is believed that the blood slipping agent of the present disclosure has an effect of lowering the viscosity of blood, such as menstrual blood in the low viscosity range. Lowering the blood viscosity presumably allows absorbed menstrual blood to more easily migrate rapidly from the top sheet to the absorbent body.

Example 4

Photomicrograph of Blood Slipping Agent-Containing Blood

Figure 4:
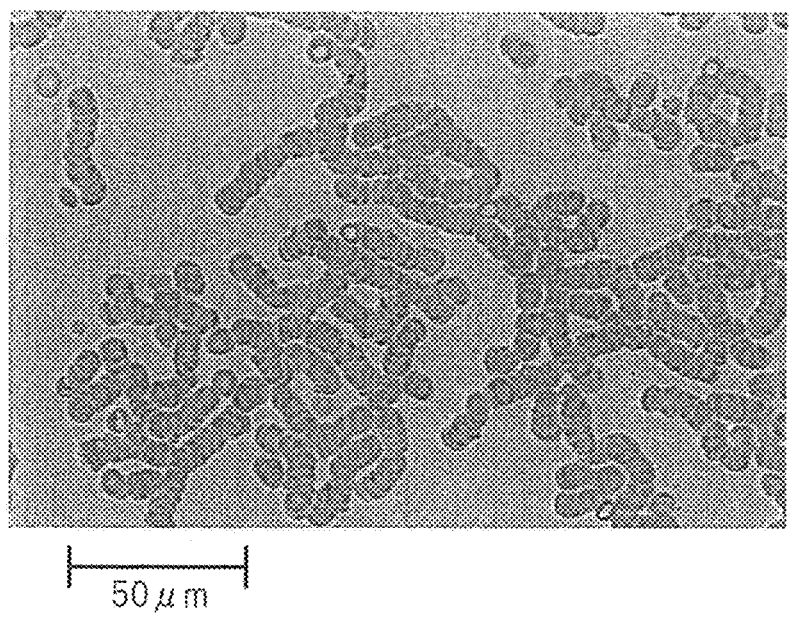
FIG. 4 is a pair of photomicrographs of menstrual blood containing and not containing a blood slipping agent.
Figure 4:
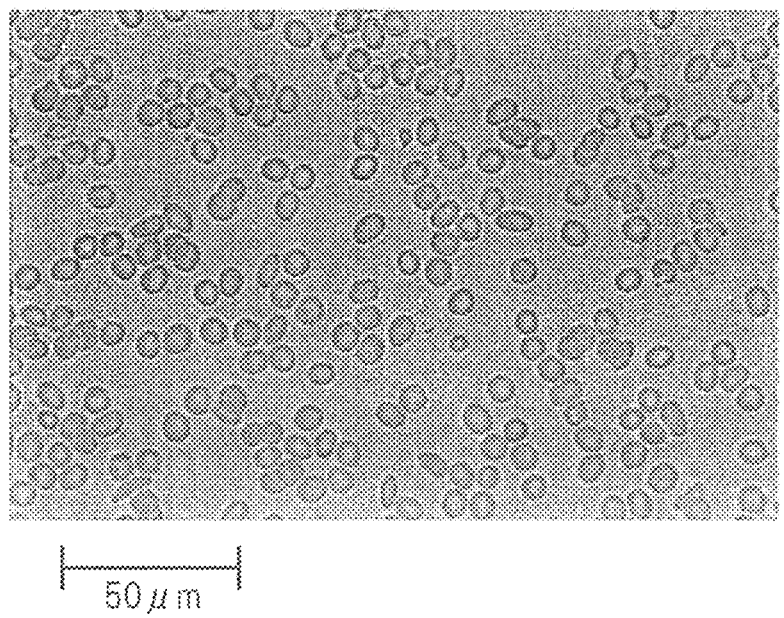
Figure 5:
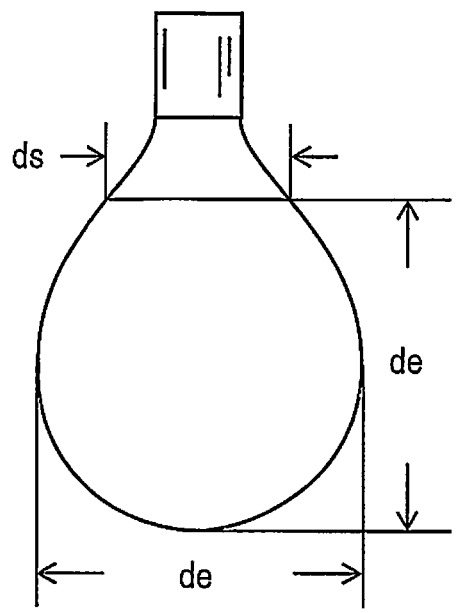
FIG. 5 is a diagram illustrating a method of measuring surface tension.

Menstrual blood was sampled from healthy volunteers onto thin plastic wrap, and PANACET 810s dispersed in a 10-fold mass of phosphate-buffered saline was added to a portion thereof to a PANACET 810s concentration of 1 mass %. The menstrual blood was dropped onto a slide glass, a cover glass was placed thereover, and the state of the erythrocytes was observed with an optical microscope. A photomicrograph of menstrual blood containing no blood slipping agent is shown in FIG. 4(a), and a photomicrograph of menstrual blood containing PANACET 810s is shown in FIG. 4(b).

From FIG. 7 it is seen that the erythrocytes formed aggregates, such as rouleaux in the menstrual blood containing no blood slipping agent, while the erythrocytes were stably dispersed in the menstrual blood containing PANACET 810s. This suggests that the blood slipping agent functions to stabilize erythrocytes in blood.

Example 5

Surface Tension of Blood Containing Blood Slipping Agent

The surface tension of blood containing a blood slipping agent was measured by the pendant drop method, using a Drop Master500 contact angle meter by Kyowa Interface Science Co., Ltd. The surface tension was measured after adding a prescribed amount of blood slipping agent to sheep defibrinated blood, and thoroughly shaking.

The measurement was accomplished automatically with a device, and the surface tension γ was determined by the following formula (see FIG. 98).

$\gamma = g \times \rho \times (de)^2 \times 1/H$ g: Gravitational constant
1/H: Correction factor determined from ds/de
ρ: Density
de: Maximum diameter
ds: Diameter at location of increase by de from dropping edge The density ρ was measured at the temperatures listed in Table 4, according to JIS K 2249-1995, "Density test methods and density/mass/volume conversion tables", "5. Vibrating density test method".

The measurement was accomplished using a DA-505 by Kyoto Electronics Co., Ltd.

The results are shown in Table 4 below.

TABLE 4

| | Blood modifying agent | | | |
|---|---|---|---|---|
| No. | Type | Amount (mass %) | Measuring temperature (° C.) | Surface tension (mN/m) |
| 1 | — | — | 35 | 62.1 |
| 2 | PANACET | 0.01 | 35 | 61.5 |
| 3 | 810s | 0.05 | 35 | 58.2 |
| 4 | | 0.10 | 35 | 51.2 |
| 5 | ELECTOL WE20 | 0.10 | 35 | 58.8 |
| 6 | PARLEAM 6 | 0.10 | 35 | 57.5 |
| 7 | — | — | 50 | 56.3 |
| 8 | WILBRITE cp9 | 0.10 | 50 | 49.1 |

Based on Table 4 it is seen that the blood slipping agent has an effect of lowering the surface tension of blood.

Lowering the surface tension of blood presumably allows absorbed blood to rapidly migrate from the top sheet to the absorbent body, without being retained between the top sheet fibers.

The present disclosure relates to the following J1 to J10.

[J1]

An absorbent article comprising a liquid-permeable top sheet, a liquid-impermeable back sheet and an absorbent body between the liquid-permeable top sheet and liquid-impermeable back sheet, wherein the liquid-permeable top sheet has an uneven structure comprising at least one projection and at least one recess on a skin contact surface thereof, and the liquid-permeable top sheet comprises a blood slipping agent having a kinematic viscosity of 0.01 to 80 mm$^2$/s at 40° C., a water holding percentage of 0.01 to 4.0 mass %, and a weight-average molecular weight of less than 1,000, on at least the projection in an excretory opening contact region.

[J2]

The absorbent article according to J1, wherein the blood slipping agent further has an IOB of 0.00-0.60.

[J3]

The absorbent article according to J1 or J2, wherein the blood slipping agent is selected from the group consisting of following items (i)-(iii), and any combination thereof:

(i) a hydrocarbon;

(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting for a hydrogen of the hydrocarbon moiety;

with the proviso that when 2 or more oxy groups are inserted in the compound of (ii) or (iii), the oxy groups are not adjacent.

[J4]

The absorbent article according to any one of J1 to J3, wherein the blood slipping agent is selected from the group consisting of following items (i')-(iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting for a hydrogen on the hydrocarbon moiety;

with the proviso that when 2 or more same or different bonds are inserted in a compound of (ii') or (iii'), the bonds are not adjacent.

[J5]

The absorbent article according to any one of J1 to J4, wherein the blood slipping agent is selected from the group consisting of following items (A)-(F), and any combination thereof:

(A) an ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety;

(B) an ether of (B1) a compound having a chain hydrocarbon moiety and 2-4 hydroxyl groups substituting for hydrogens on the chain hydrocarbon moiety, and (B2) a compound having a chain hydrocarbon moiety and 1 hydroxyl group substituting for a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting for hydrogens on the chain hydrocarbon moiety, and (C2) a compound having a chain hydrocarbon moiety and 1 hydroxyl group substituting for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy $C_3$-$C_6$ alkylene glycol, or ester or ether thereof; and (F) a chain hydrocarbon.

[J6]

The absorbent article according to any one of J1 to J5, wherein the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, ($e_2$) an ester of a polyoxy $C_3$-$C_6$ alkylene glycols and at least one fatty acid, ($e_3$) an ether of a polyoxy $C_3$-$C_6$ alkylene glycol and at least one aliphatic monohydric alcohol, and ($f_1$) a chain alkane, and any combination thereof.

[J7]
The absorbent article according to any one of J1 to J6, wherein the liquid-permeable top sheet has on the skin contact surface a ridge-furrow structure including a plurality of ridges and a plurality of furrows, with at least the ridges containing the blood slipping agent.

[J8]
The absorbent article according to any one of J1 to J7, wherein the liquid-permeable top sheet has embossed sections formed by embossing at least the liquid-permeable top sheet.

[J9]
The absorbent article according to any one of J1 to J8, wherein the liquid-permeable top sheet is a nonwoven fabric or woven fabric, and the blood slipping agent is attached to the surfaces of the fibers of the nonwoven fabric or woven fabric.

[J10]
The absorbent article according to any one of J1 to J9, wherein the absorbent article is a sanitary napkin or panty liner.

REFERENCES SIGNS LIST

1 Sanitary napkin
2 Top sheet
3 Absorbent body
4 Side sheet
5 Embossed section
6 Back sheet
7 Projection
8 Recess
9 Skin contact surface
10 Blood slipping agent
11, 11', 11" Menstrual blood

The invention claimed is:
1. An absorbent article comprising a liquid-permeable top sheet, a liquid-impermeable back sheet and an absorbent body between the liquid-permeable top sheet and liquid-impermeable back sheet,
wherein the liquid-permeable top sheet has an uneven structure comprising at least one projection and at least one recess on a skin contact surface thereof, and
wherein the liquid-permeable top sheet comprises a coating consisting essentially of a blood slipping agent having a kinematic viscosity of 0.01 to 80 mm$^2$/s at 40° C., a water holding percentage of 0.01 to 4.0 mass %, and a weight-average molecular weight of less than 1,000, on at least the projection in an excretory opening contact region, and the coating is configured to slip down from the skin contact surface, through the liquid-permeable top sheet to the absorbent body along with menstrual blood.

2. The absorbent article according to claim 1, wherein the blood slipping agent further has an Inorganic Organic Balance (JOB) of 0.00-0.60.

3. The absorbent article according to claim 1, wherein the blood slipping agent is selected from the group consisting of following items (i)-(iii), and any combination thereof:
(i) a hydrocarbon;
(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting for a hydrogen of the hydrocarbon moiety;
with the proviso that when 2 or more oxy groups are inserted in the compound of (ii) or (iii), the oxy groups are not adjacent.

4. The absorbent article according to claim 1, wherein the blood slipping agent is selected from the group consisting of following items (i')-(iii'), and any combination thereof:
(i') a hydrocarbon;
(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
(iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting for a hydrogen on the hydrocarbon moiety;
with the proviso that when 2 or more same or different bonds are inserted in a compound of (ii') or (iii'), the bonds are not adjacent.

5. The absorbent article according to claim 1, wherein the blood slipping agent is selected from the group consisting of following items (A)-(F), and any combination thereof:
(A) an ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety;
(B) an ether of (B1) a compound having a chain hydrocarbon moiety and 2-4 hydroxyl groups substituting for hydrogens on the chain hydrocarbon moiety, and (B2)

a compound having a chain hydrocarbon moiety and 1 hydroxyl group substituting for a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting for hydrogens on the chain hydrocarbon moiety, and (C2) a compound having a chain hydrocarbon moiety and 1 hydroxyl group substituting for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy C3-C6 alkylene glycol, or ester or ether thereof; and (F) a chain hydrocarbon.

6. The absorbent article according to claim 1, wherein the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy C3-C6 alkylene glycol, ($e_2$) an ester of a polyoxy C3-C6 alkylene glycols and at least one fatty acid, ($e_3$) an ether of a polyoxy C3-C6 alkylene glycol and at least one aliphatic monohydric alcohol, and ($f_1$) a chain alkane, and any combination thereof.

7. The absorbent article according to claim 1, wherein the at least one projection is a plurality of ridges, and the at least one recess is a plurality of furrows.

8. The absorbent article according to claim 1, wherein the liquid-permeable top sheet has embossed sections formed by embossing at least the liquid-permeable top sheet.

9. The absorbent article according to claim 1, wherein the liquid-permeable top sheet is a nonwoven fabric or woven fabric, and the blood slipping agent is attached to the surfaces of the fibers of the nonwoven fabric or woven fabric.

10. The absorbent article according to claim 1, wherein the absorbent article is a sanitary napkin or panty liner.

* * * * *